United States Patent [19]

Gerster et al.

[11] Patent Number: 5,605,899
[45] Date of Patent: Feb. 25, 1997

[54] 1-SUBSTITUTED, 2-SUBSTITUTED 1H-IMIDAZO[4,5-C]QUINOLIN-4-AMINES

[75] Inventors: John F. Gerster, Woodbury; Stephen L. Crooks, Mahtomedi, both of Minn.; Kyle J. Lindstrom, Houlton, Wis.

[73] Assignee: Minnesota Mining and Manufacturing Company, St. Paul, Minn.

[21] Appl. No.: 353,802

[22] Filed: Dec. 12, 1994

Related U.S. Application Data

[60] Division of Ser. No. 938,295, Aug. 28, 1992, Pat. No. 5,389,640, which is a continuation-in-part of Ser. No. 838,475, Feb. 19, 1992, abandoned, which is a continuation-in-part of Ser. No. 687,326, Apr. 18, 1991, abandoned, which is a continuation-in-part of Ser. No. 662,926, Mar. 1, 1991, abandoned.

[51] Int. Cl.$^6$ ............... C07D 413/06; C07D 471/04; A61K 31/44; A61K 31/47
[52] U.S. Cl. ............... 514/232.8; 514/293; 546/82; 544/126; 552/10
[58] Field of Search ............... 546/82; 514/293, 514/232.8; 544/126; 552/10

[56] References Cited

U.S. PATENT DOCUMENTS

| | | | |
|---|---|---|---|
| 4,689,338 | 8/1987 | Gerster | 514/293 |
| 4,698,348 | 10/1987 | Gerster | 514/293 |
| 4,929,624 | 5/1990 | Gerster | 514/293 |
| 4,988,815 | 1/1991 | Andre et al. | 546/159 |
| 4,994,468 | 2/1991 | Suzuki et al. | 514/293 |
| 5,010,084 | 4/1991 | Suzuki et al. | 514/293 |
| 5,175,296 | 12/1992 | Gerster | 546/82 |
| 5,266,575 | 11/1993 | Gerster et al. | 514/293 |
| 5,389,640 | 2/1995 | Gerster et al. | 514/293 |
| 5,395,937 | 3/1995 | Nikolaides et al. | 546/82 |

OTHER PUBLICATIONS

Bachman et al., J. Org. Chem. 15, 1278–1284 (1950).
Jain et al., J. Med. Chem. 11, pp. 87–92 (1968).
Baranov et al., Chem. Abs. 85, 94362 (1976).
Berenyi et al., J. Heterocyclic Chem. 18, 1537–1540 (1981).
Van Galen et al., J. Med. Chem. 34, 1202 (1991).

*Primary Examiner*—Alan L. Rotman
*Attorney, Agent, or Firm*—Gary L. Griswold; Walter N. Kirn; Ted K. Ringsred

[57] ABSTRACT

1-substituted, 2-substituted 1H-imidazo[4,5-c]-quinolin-4-amines are disclosed. These compounds function as antiviral agents, they induce biosynthesis of interferon, and they inhibit tumor formation in animal models. This invention also provides intermediates for preparing such compounds, pharmaceutical compositions containing such compounds, and pharmacological methods of using such compounds.

36 Claims, No Drawings

1-SUBSTITUTED, 2-SUBSTITUTED 1H-IMIDAZO[4,5-C]QUINOLIN-4-AMINES

This is a division of application Ser. No. 07/938,295 filed Aug. 28, 1992, now U.S. Pat. No. 5,389,640, which is a continuation-in-part of commonly assigned application U.S. Ser. No. 07/838,475, filed Feb. 19, 1992, now abandoned, which is a continuation-in-part of commonly assigned copending application U.S. Ser. No. 07/687,326, filed Apr. 18, 1991, now abandoned, which is a continuation-in-part of commonly-assigned copending application U.S. Ser. No. 07/662,926, filed on Mar. 1, 1991, now abandoned.

BACKGROUND OF THE INVENTION

1. Field of the Invention

This invention relates to 1H-imidazo[4,5-c]quinoline compounds. In other aspects, this invention relates to antiviral 1H-imidazo[4,5-c]quinolin-4-amines, intermediates for the preparation of such compounds, pharmaceutical compositions containing such compounds, and pharmacological methods of using such compounds.

2. Description of the Related Art

The first reliable report of the 1H-imidazo[4,5-c]quinoline ring system, Backman et al., J. Org. Chem. 15, 1278–1284 (1950), describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines have been reported. For example, Jain et al., J. Med. Chem. 11, pp. 87–92 (1968), has synthesized the compound 1-[2-(4-piperidyl)ethyl]-1H-imidazo[4,5-c]quinoline as a possible anticonvulsant and cardiovascular agent. Also, Baranov et al., Chem. Abs. 85, 94362 (1976), has reported several 2-oxoimidazo[4,5-c]quinolines, and Berenyi et al., J. Heterocyclic Chem. 18, 1537–1540 (1981), has reported certain 2-oxoimidazo[4,5-c]quinolines.

Certain antiviral 1H-imidazo[4,5-c]quinolin-4-amines are described in U.S. Pat. No. 4,689,338 (Gerster). These compounds are substituted on the 1-position by alkyl, hydroxyalkyl, acyloxyalkyl, benzyl, phenylethyl or substituted phenylethyl, and at the 2-position with hydrogen, alkyl, benzyl, or substituted benzyl, phenylethyl or phenyl. Furthermore, these compounds are known to induce interferon biosynthesis. Other antiviral 1H-imidazo[4,5-c]quinolin-4-amines, substituted on the 1-position by alkenyl substituents, are described in U.S. Pat. No. 4,929,624 (Gerster).

U.S. Pat. No. 4,698,348 (Gerster) discloses 1H-imidazo[4,5-c]quinolines that are active as bronchodilators, such as 4-substituted 1H-imidazo[4,5-c]quinolines wherein the 4-substituent is, inter alia, hydrogen, chloro, alkylamino, or dialkylamino, and the 2-substituent is, inter alia, hydroxyalkyl, aminoalkyl, or alkanamidoalkyl. Said patent also discloses 3-amino and 3-nitro quinoline intermediates substituted at the 4-position by hydroxyalkylamino or cyclohexylmethylamino, and 1H-imidazo[4,5-c]quinoline N-oxide intermediates substituted at the 2-position with, inter alia, hydroxyalkyl, aminoalkyl, or alkanamidoalkyl.

DETAILED DESCRIPTION OF THE INVENTION

This invention provides compounds of Formula I:

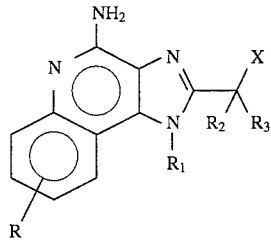

wherein $R_1$ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that if said benzene ring is substituted by two of said moieties, then the moieties together contain no more than six carbon atoms;

$R_2$ and $R_3$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, hydroxyalkyl of one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, and alkylthio of one to about four carbon atoms; and R is selected from the group consisting of hydrogen, straight chain or branched chain alkoxy containing one to about four carbon atoms, halogen, and straight chain or branched chain alkyl containing one to about four carbon atoms;

or a pharmaceutically acceptable acid addition salt thereof.

This invention provides intermediate compounds of Formula V(a)

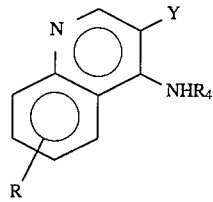

wherein R is as defined above, Y is —NO$_2$ or —NH$_2$, and R$_4$ is alkoxyalkyl wherein the alkoxy moiety contains one to about four carbon atoms and the alkyl moiety contains two to about six carbon atoms.

This invention provides intermediate compounds of Formula VII(a)

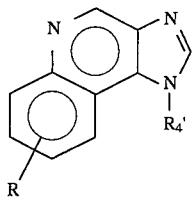

wherein R is as defined above in connection with Formula V(a) and R$_4$' is alkoxy alkol wherein the alkoxy moiety contains one to about four carbon atoms and the alkyl moiety contains one to about six carbon atoms.

This invention provides intermediate compounds of Formula IX(a)

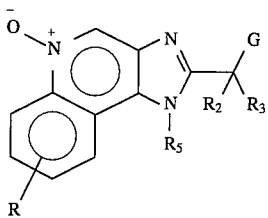

wherein

R, R$_2$, and R$_3$ are as defined above;

R$_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl, or phenyl substituent being optionally substituted on the benzene ring by one or two moieties independently selected from the group consisting of alkyl of one to about four carbon atoms, alkoxy of one to about four carbon atoms, and halogen, with the proviso that if said benzene ring is substituted by two of said moieties, then the moieties together contain no more than six carbon atoms; and G is selected from the group consisting of, alkoxy containing one to about four carbon atoms, alkoxyalkyl wherein the alkoxy moiety contains one to about four carbon atoms and the alkyl moiety contains one to about four carbon atoms, alkylamido wherein the alkyl group contains one to about four carbon atoms, azido, chloro, 1-morpholino, 1-pyrrolidino, alkylthio of one to about four carbon atoms, alkanoyloxy, alkanoyloxyalkyl wherein the alkyl moiety contains one to about four carbon atoms, and aroyloxy, with the proviso that when G is alkylamido then R$_5$ is alkenyl, substituted alkenyl, or alkoxyalkyl.

Further this invention provides compounds of Formula XI(a)

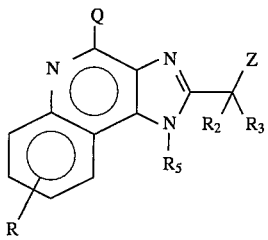

wherein

R, R$_2$, R$_3$ and R$_5$ are as defined above,

Z is selected from the group consisting of alkoxy containing one to about four carbon atoms, alkoxyalkyl wherein the alkoxy moiety contains one to about four carbon atoms and the alkyl moiety contains one to about four carbon atoms, hydroxyalkyl containing one to about four carbon atoms, oxoalkyl containing two to about four carbon atoms, alkanoyloxyalkyl wherein the alkyl moiety contains one to about four carbon atoms, alkylamido wherein the alkyl group contains one to about four carbon atoms, substituted amino wherein the substituent is alkyl or hydroxyalkyl of one to about four carbon atoms, azido, chloro, 1-morpholino, 1-pyrrolidino, alkylthio of one to about four carbon atoms, hydroxy, alkanoyloxy, and aroyloxy; and Q is selected from the group consisting of hydrogen, chloro, and R$_i$—E—NH— wherein R$_i$ is an organic group substantially inert to quinoline N-oxides and E is a hydrolytically active functional group, with the proviso that when Q is R$_i$—E—NH—, then Z is other than hydroxy, substituted amino, or hydroxyalkyl, and with the further proviso that when Q is hydrogen or chloro and Z is alkylamido or hydroxyalkyl, then R$_5$ is alkenyl, substituted alkenyl, or alkoxyalkyl.

R$_1$ of Formula I preferably contains two to about ten carbon atoms. More preferably R$_1$ contains two to about eight carbon atoms. Most preferably, R$_1$ is 2-methylpropyl or benzyl.

X of Formula I is preferably azido, hydroxy, ethoxy, methoxy, 1-morpholino, or methylthio, particularly in embodiments wherein $R_1$ is 2-methylpropyl, 2-hydroxy-2-methylpropyl, or benzyl.

Other substituents in compounds of Formula I that contain an alkyl radical (e.g., R when R is alkoxy or alkyl, or X when X is alkylamido) preferably contain two carbon atoms or, more preferably, one carbon atom in each alkyl radical.

It is preferred that R of Formula I be hydrogen.

Most preferred compounds of Formula I include 4-amino-α-butyl-1-(2-methylpropyl)-1H-imidazo[4,5-c]quinoline-2-methanol hemihydrate, 4-amino-α,α-dimethyl-2-ethoxymethyl-1H-imidazo[4,5-c]quinoline-1-ethanol, 2-ethoxymethyl-1-(2-methylpropyl)-1H-imidazo[4,5-c]quinolin-4-amine, and 4-amino-1-phenylmethyl-1H-imidazo[4,5-c]quinoline-2-methanol.

A compound of the invention can be prepared as described in the Reaction Scheme below, wherein R, $R_1$, $R_2$, $R_3$, and X are as defined above and wherein P is a hydroxyl protecting group that can subsequently be removed, such as alkanoyloxy (e.g., acetoxy), or aroyloxy (e.g., benzoyloxy), and $R_5$ is as defined for $R_1$ above absent hydroxyalkyl and hydrogen.

Many quinolines of Formula III are known compounds (see, for example, U.S. Pat. No. 3,700,674 and references cited therein). Those that are not known can be prepared by known methods, for example, from 4-hydroxy-3-nitroquinolines as illustrated in step (1) of Scheme I. Step (1) can be conducted by reacting the 4-hydroxy-3-nitroquinoline of Formula II with a chlorinating agent such as thionyl chloride or phosphorus oxychloride. The reaction is preferably conducted in N,N-dimethylformamide, optionally in the presence of methylene chloride, and is preferably accompanied by heating. Preferably, a large molar excess of phosphorus oxychloride is avoided. Use of about 1-2 moles of phosphorus oxychloride per mole of the 4-hydroxy-3-nitroquinoline of Formula II has been found to be particularly preferable.

In step (2) a 3-nitro-4-chloroquinoline of Formula III is reacted by heating with an amine of the formula $R_5NH_2$, wherein $R_5$ is as defined above, in a suitable solvent such as water, dichloromethane, or tetrahydrofuran, to provide a quinoline of Formula IV. Steps (1) and (2) can be combined such that the 3-nitro-4-chloroquinoline need not be isolated prior to reaction with the compound of the formula $R_5NH_2$. Such a reaction is exemplified in Example 134 and Example 188 (Step A) of U.S. Pat. No. 4,689,338, the disclosure of which is incorporated herein by reference.

A compound of Formula IV is reduced in step (3) preferably using a catalyst such as platinum on carbon, to provide a compound of Formula V. This can be carried out conveniently on a Parr apparatus in an inert solvent such as toluene or a lower alkanol.

In step (4) an intermediate compound of Formula V is reacted with (i) a carboxylic acid of the formula,

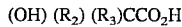
(OH) $(R_2)$ $(R_3)CCO_2H$ or (ii) a trialkyl ortho ester of the formula,

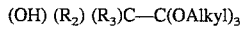
(OH) $(R_2)$ $(R_3)C$—$C(OAlkyl)_3$ wherein "alkyl" is a straight chain or branched chain alkyl group containing one to about four carbon atoms, or (iii) a combination of such a carboxylic acid with such a trialkyl ortho ester to provide a compound of Formula VI. In any case, the reaction can be carried out by heating, e.g., at about 130° C., in the presence of an acid, preferably a carboxylic acid of the formula

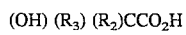
(OH) $(R_3)$ $(R_2)CCO_2H$

An alternate method of providing the 2-substituted imidazo ring is illustrated in steps (5) and (6). Step (5) involves a reaction similar to that described in connection with step (4), but involving formic acid or a trialkylorthoformate to form an intermediate of Formula VII. The intermediate of Formula VII can then be deprotonated by a strong base (e.g., an alkyllithium such as n-butyllithium) and reacted with a compound of the formula

$$\underset{R_2CR_3}{\overset{O}{\|}}$$

to form an intermediate of Formula VI.

Step (7) involves protecting the hydroxyl group with a removable protecting group such as an alkanoyloxy group (e.g., acetoxy) or an aroyloxy group (e.g., benzoyloxy). In instances wherein a hydroxyl group is present in the 1-substituent, it too can be protected in step (7) and later removed as appropriate when it will no longer interfere with subsequent reactions. Suitable protecting groups and reactions for their placement and removal are well known to those skilled in the art. See, for example, U.S. Pat. No. 4,689,338 (Gerster), Examples 115–123.

Step (8) provides an intermediate of Formula IX, through oxidation of a compound of Formula VIII with a conventional oxidizing agent that is capable of forming N-oxides. Preferred oxidizing agents include peroxyacids and hydrogen peroxide. Heating is generally employed to accelerate the rate of reaction.

In step (9) an N-oxide of Formula IX is heated in the presence of a suitable chlorinating agent such as phosphorus oxychloride to provide a chlorinated intermediate of Formula X.

In step (10) the 4-chloro group is replaced by a 4-amino group and the protecting group P is removed to provide a compound of Formula XII (a subgenus of Formula I). The amination reaction is carried out in the presence of ammonium hydroxide or, preferably, ammonia. Preferably the intermediate of Formula X is heated at 125° to 175° C. under pressure for 6–24 hours. Preferably the reaction is conducted in a sealed reactor in the presence of either ammonium hydroxide or a solution of ammonia in an alkanol, (e.g., preferably about 5% to about 15% ammonia in methanol).

A compound of Formula XII can also be prepared by way of step (9a) of the Reaction Scheme. Step (9a) involves (i) reacting a compound of Formula IX with an acylating agent; (ii) reacting the product with an aminating agent; and (iii) isolating the compound of Formula XII. Part (i) of step (9a) involves reacting an N-oxide with an acylating agent. Suitable acylating agents include alkyl- or arylsulfonyl chlorides (e.g., benzenesulfonyl chloride, methanesulfonyl chloride, p-toluenesulfonyl chloride). Arylsulfonyl chlorides are preferred. p-Toluenesulfonyl chloride is most preferred. Part (ii) of step (9a) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, and ammonium phosphate). Ammonium hydroxide is preferred. The reaction of step (9a) is preferably carried out by dissolving the N-oxide of Formula IX in an inert solvent such as methylene chloride, adding the aminating agent to the solution, and then adding the acylating agent. Preferred conditions involve cooling to about 0° C. to about 5° C. during the addition of the acylating agent. Heating or cooling can be used to control the rate of reaction. Step (9a) also involves removal of protecting group P as discussed above in connection with step (7). A further alternative method of preparing a compound of Formula XII is shown in steps (11) and (12).

Step (11) involves reacting an N-oxide with an isocyanate wherein the isocyanato group is bonded to a hydrolytically active functional group. The term "hydrolytically active functional group" as used herein designates any functional group that is capable of being subjected to a nucleophilic displacement reaction in step (12) of the Reaction Scheme. Exemplary hydrolytically active functional groups include carbonyl

A particular class of such isocyanates is isocyanates of the formula $R_i$—E—NCO, wherein $R_i$ is an organic group substantially inert to quinoline N-oxides under the conditions of step (11) and E is a hydrolytically active functional group. Suitable $R_i$ groups are easily selected by those skilled in the art. Preferred groups $R_i$ include alkyl, aryl, alkenyl, and combinations thereof. Particular preferred isocyanates include aroyl isocyanates such as benzoylisocyanate. The reaction of the isocyanate with the N-oxide is carried out under substantially anhydrous conditions by adding the isocyanate to a solution of the N-oxide in an inert

REACTION SCHEME

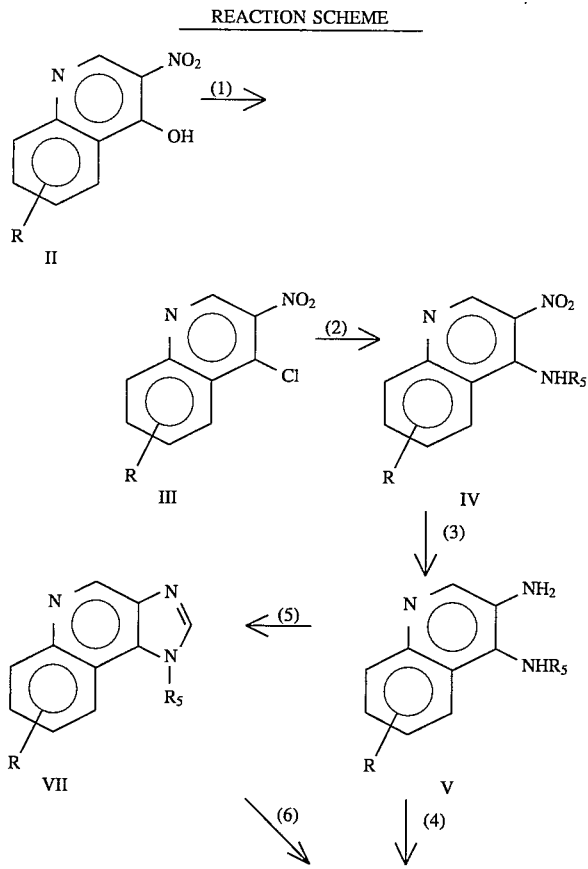

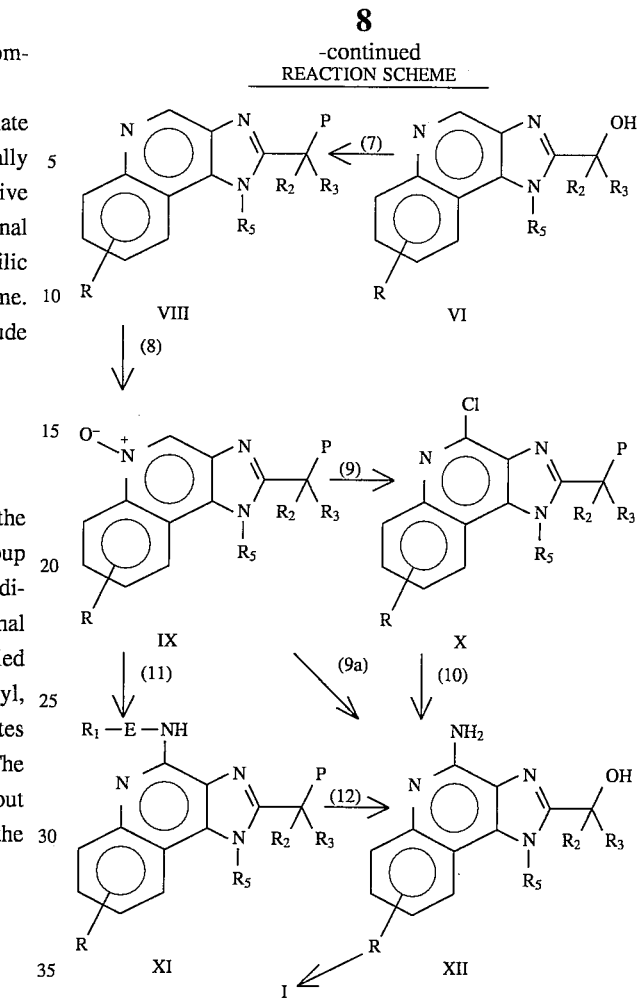

solvent such as dichloromethane. The resulting 4-substituted compound of Formula XI can be isolated by removal of the solvent.

Step (12) of the Reaction Scheme involves hydrolysis of a compound of Formula XI. The term "hydrolysis" as used herein designates not only nucleophilic displacement with water but also displacement with other nucleophilic compounds. Such a reaction can be carried out by general methods well known to those skilled in the art, e.g., by heating in the presence of a nucleophilic solvent such as water or a lower alkanol optionally in the presence of a catalyst such as an alkali metal hydroxide or lower alkoxide.

In steps (9a), (10) or (12) a compound comprising a protecting group such as acetoxy, benzoyloxy, or the like, is deprotected to afford a compound comprising a hydroxyl group. A hydroxyl-containing compound of Formula I can be converted or elaborated by methods well known to the skilled in the art to afford a further compound of Formula I. For example, reaction with thionyl chloride will provide a compound of Formula I wherein X is chloro. Reaction of this compound with a nucleophile such as sodium azide, pyrrolidine, methanethiol, or morpholine will afford a compound of Formula I wherein X is azido, 1-pyrrolidino, thiomethyl, or 1-morpholino, respectively. Reduction of an azido compound provides a compound of Formula I wherein X is amino. Such an amino compound can be acylated to form a compound wherein X is alkylamido.

Some compounds of Formula I can be prepared by a similar reaction scheme wherein the group X is introduced directly in step (4) in which case hydroxyalkyl substituents will be tolerated at the 1-position with appropriate use of the various protection and deprotection steps.

Substituents at the 2-position can be introduced by reacting a compound of Formula XIII

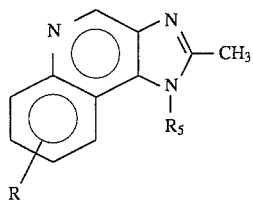

XIII wherein R and $R_5$ are as defined above, with a lithiating agent such a lithium diisopropylamide or n-butyllithium in a polar aprotic solvent to afford a compound lithiated on the 2-methyl group. The lithiated compound can then be reacted with an appropriate reagent containing a leaving group capable of being displaced by the lithiated 2-methyl group, such as, e.g., chloromethylmethylether or N-methoxy-N-methylacetamide, in order to elaborate the 2-methyl group. Such compounds can then be carried on as appropriate to compounds of Formula I.

A further alternate process for preparing certain compounds of Formula I involves as a first step the preparation of a 3-amino-4-(substituted) amino-2-chloroquinoline according to the method set forth in U.S. Pat. No. 4,988,815 (Andre et al., incorporated herein by reference). This compound is then reacted in a polar aprotic solvent with a carboxylic acid halide, which reacts at the 3-amino group to afford the corresponding 3-carboxamido-4-(substituted)amino-2-chloroquinoline. This compound is then reacted with ammonia, e.g., in a hydroxylic solvent such as methanol, at an elevated temperature (e.g., 100°–150° C.) to effect 1) cyclization and 2) amination at the 4-position, resulting in a 1-substituted, 2-substituted 1H-imidazo[4,5-c]quinolin-4-amine.

While not all compounds of Formula I can be prepared by the illustrated reaction scheme, known schemes can be easily adapted by those skilled in the art in order to prepare compounds other than those exemplified herein. For example, compounds wherein $R_1$ is alkenyl can be prepared using the general schemes or adaptations thereof set forth in U.S. Pat. No. 4,929,624 (Gerster et al.) and compounds wherein $R_1$ is hydrogen can be prepared using the general schemes or adaptations thereof set forth in commonly assigned copending application Ser. No. 07/484,761 (Gerster), both being incorporated herein by reference. A further synthetic scheme that can be used by those skilled in the art in the preparation of some of the compounds of the invention is disclosed in U.S. Pat. No. 4,988,815 (Andre' et al.) incorporated herein by reference. Further, those skilled in the art will recognize that alteration of reaction sequence and utilization of conventional synthetic alternatives will allow the preparation of the compounds of the invention not amenable to the illustrated scheme.

The product compound of Formula I can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, or by dissolution in an appropriate solvent (such as methanol) and re-precipitation by addition of a second solvent in which the compound is insoluble.

A compound of Formula I can be used as an antiviral agent itself or it can be used in the form of a pharmaceutically acceptable acid-addition salt such as a hydrochloride, dihydrogen sulfate, trihydrogen phosphate, hydrogen nitrate, methanesulfonate or a salt of another pharmaceutically acceptable acid. A pharmaceutically acceptable acid-addition salt of a compound of Formula I can be prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in a pharmaceutically acceptable vehicle, such as water or polyethylene glycol, along with suitable adjuvants, excipients, and the like. Particular formulations will be easily selected by those skilled in the art. Suitable formulations for topical application include creams, ointments and like formulations known to those skilled in the art. Formulations generally contain less than 10% by weight of a compound of Formula I, preferably about 0.1% to 5% by weight of a compound of Formula I.

The compounds of Formula I exhibit antiviral activity in mammals. They can therefore be used to control viral infections. For example, a compound of Formula I can be used as an agent to control infections in mammals caused by Type II Herpes simplex virus. Compounds of Formula I can also be used to treat a herpes infection by oral, topical, or intraperitoneal administration.

A number of compounds of Formula I were tested and found to induce biosynthesis of interferon in human cells and in mice. Furthermore, a number of compounds of Formula I were tested and found to inhibit tumors in mice. The test methods and results are set forth below. These results suggest that at least certain compounds of the invention might be useful in treating other diseases such as rheumatoid arthritis, warts, eczema, Hepatitis B, psoriasis, multiple sclerosis, essential thrombocythaemia, cancer such as basal cell carcinoma, and other neoplastic diseases.

In the following Examples, all reactions were run with stirring under an atmosphere of dry nitrogen unless otherwise indicated. The particular materials and amounts thereof recited in the Example, as well as other conditions and details, should not be construed to unduly limit the invention.

EXAMPLE 1

1-(2-Methylpropyl)-1H-imidazo[4,5-c]quinoline-2-methanol

3-Nitro-4-(2-methylpropylamino)quinoline (36.8 g; 0.15 mol) was added to a mixture of ethyl acetate (300 mL), 5% Pt/C (about 1 g), and magnesium sulfate (30 g). The mixture was hydrogenated at about 50 psi initial pressure. When hydrogenation was complete the solids were filtered from the mixture and the ethyl acetate was evaporated. The resulting intermediate diamine was mixed with glycolic acid (26.9 g; 0.35 mol) and the mixture was heated at 150°–160° C. for about 3 hr with occasional manual stirring. The reaction mixture was then dissolved in dilute hydrochloric acid and treated with decolorizing carbon, and the solids were filtered from the mixture. The filtrate was made basic with ammonium hydroxide to precipitate the product as a greenish solid. The solid was filtered and dried to give 34.3 g (89.6%) of crude product. The solid was reprecipitated a second time as above and the product recrystallized from ethyl acetate to give greenish crystals, m.p. 165°–168° C.

Analysis: Calculated: C, 70.6; H, 6.7; N, 16.5. Found: C, 70.4, H, 6.7; N, 16.3.

EXAMPLE 2

1-(2-Methylpropyl)-1H-imidazo[4,5-c]quinoline-2-methyl Acetate 1-(2-Methylpropyl)-1H-imidazo[4,5-c]quinoline-2-methanol (51.4 g; 0.2 mol, Example 1) was dissolved in dichloromethane (500 mL) containing triethylamine (30.9 mL; 0.22 mol). The solution was stirred at room temperature while acetyl chloride was added dropwise. The resulting solution was stirred at room temperature for about 24 hr and then washed with water and aqueous sodium bicarbonate. The organic layer was dried over magnesium sulfate and evaporated to yield 58.1 g (97%) of the acetate as a brownish solid. The product was recrystallized from ethyl acetate to give a tan solid m.p. 147°–154° C. Analysis: Calculated: C, 68.7; H, 6.4; N, 14.1. Found: C, 68.1; H, 6.4; N, 13.8.

EXAMPLE 3

1-(2-Methylpropyl)-1H-imidazo[4,5-c]quinoline-2-methyl Benzoate

The compound was prepared from 1-(2-methylpropyl)-1H-imidazo[4,5-c]quinoline-2-methanol (Example 1) using benzoyl chloride in the general method of Example 2.

EXAMPLE 4

2-Acetoxymethyl-1-(2-methylpropvl)-1H-imidazo[4,5-c]quinoline 5N Oxide 1-(2-Methylpropyl)-1H-imidazo[4,5-c]quinoline-2-methyl acetate (63.0 g; 0.21 mol, Example 2) was suspended in ethanol (475mL) and 32% peracetic acid (89 mL; 0.42 mol) was added to the mixture. The mixture was heated at 50° C. with stirring for 2 hr. The solid dissolved upon heating and after about 1½ hr a heavy precipitate formed. The precipitate was filtered from the mixture and dried to yield 33.7 g of the N-oxide. The filtrate was concentrated to 100 mL and an additional 15.2 g of solid was collected. A total crude yield of 48.9 g (74.3%) was obtained. The material was recrystallized from ethanol to give pale yellow crystals m.p. 233°–240° C. Analysis: Calculated: C, 65.1; H, 6.1; N, 13.4. Found: C, 64.6; H, 6.1; N, 13.2.

EXAMPLE 5

2-Benzoyloxymethyl-1-(2-methylpropyl)-1H-imidazo[4,5-c]quinoline 5N Oxide

The compound was prepared using 1-(2-methylpropyl)-1H-imidazo[4,5-c]quinoline-2-methyl benzoate (Example 3) in the method of Example 4 and recrystallized from ethyl acetate to give a pure product, m.p. 192°–195° C. Analysis: Calculated: C, 70.4; H, 5.6; N, 11.2. Found: C, 70.6; H, 5.7; N, 11.2.

EXAMPLE 6

4-Chloro-1-(2-methylpropyl)-1H-imidazo[4,5-c]quinoline-2-methyl Acetate

2-Acetoxymethyl-1-(2-methylpropyl)-1-Himidazo[4,5-c]quinoline 5N oxide (48.9 g; 0.156 mol, Example 4) was suspended in dichloromethane (500 mL) and phosphorous oxychloride (17.5 mL; 0.187 mol) was added dropwise to the stirred suspension. The vigorous reaction was controlled by adjusting the rate of addition. When addition was complete the mixture was stirred at reflux for 1 hr. The mixture was then cautiously neutralized with sodium bicarbonate. All solid dissolved in the dichloromethane. The organic layer was separated, dried over magnesium sulfate, and evaporated to yield 43.6 g (84.2%) of crude product. A small amount was purified by silica gel flash chromatography (ethyl acetate as eluent) and recrystallized from ethyl acetate to give a pure sample m.p. 182°–188° C. Analysis: Calculated: C, 61.5; H, 5.5; N, 12.7. Found: C, 61.5; H, 5.4; N, 12.6.

EXAMPLE 7

4-Chloro-1-2-methylpropyl)-1H-imidazo[4,5-c]quinoline-2-methyl Benzoate

The compound was prepared using 2-benzoyloxymethyl-1-(2-methylpropyl)-1H-imidazo[4,5c]quinoline-5N-oxide (Example 5) in the method of Example 6 and recrystallized from ethyl acetate/hexane for analysis and characterization. m.p. 143°–150° C. Analysis: Calculated: C, 67.1; H, 5.1; N, 10.7. Found: C, 67.2; H, 5.1; N, 10.6.

EXAMPLE 8

4-Chloro-1-2-methylpropyl)-1H-imidazo[4,5-c]quinoline-2-methanol

4-Chloro-1-(2-methylpropyl)-1H-imidazo[4,5-c]quinoline-2-methyl benzoate (14.3 g; 0.36 mol, Example 7) was suspended in dry methanol (350 mL). The mixture was made basic (pH 10) with 25% sodium methoxide. The mixture was stirred at room temperature for 5 hr after which time only a trace of starting material was detected by silica gel TLC (ethyl acetate eluent). The mixture was made acidic with acetic acid and then concentrated to dryness. The residue was slurried in ether. The solid was filtered from the mixture and then suspended in aqueous sodium hydroxide. The product was filtered from the mixture, washed with water, and dried to yield 7.5 g (71.4%) of tan solid. The product was recrystallized from ethanol to yield 4.8 g of pure product m.p. 162°–166° C. Analysis: Calculated: C, 62.2; H, 5.6; N, 14.5. Found: C, 62.2; H, 5.6; N, 14.3.

EXAMPLE 9

4-Amino-1-(2-methylpropyl)-1H-imidazo[4,5-c]quinoline-2-methanol

4-Chloro-1-(2-methylpropyl)-1H-imidazo[4,5-c]quinoline-2-methyl benzoate (5.0 g; 0.13 mol, Example 7) was added to 15% methanolic ammonia (50 mL). The mixture was heated in a Parr bomb for 7 hr at 175° C. The resulting solution was evaporated to reduce the volume. A sticky solid crystallized from the solution. The solid was filtered from the mixture and slurried in aqueous sodium bicarbonate solution. The resulting solid was filtered from the mixture, washed with water, and dried to yield 2.1 g (61.7%) of crude product which was recrystallized from ethanol several times to yield pure product m.p. 226°–231° C. Analysis: Calculated: C, 66.6: H, 6.7; N, 20.7. Found: C, 66.4; H, 6.5; N, 20.4.

EXAMPLE 10

2-Chloromethyl-1-(2-methylpropyl)-1H-imidazo[4,5-c]quinolin-4-amine Hydrochloride 4-Amino-1-(2-methylpropyl)-1H-imidazo[4,5-c]quinoline-2-methanol (5.0 g; 0.0185 mol, Example 9) was added in small portions to vigorously stirred thionyl chloride (25 mL). The resulting mixture was stirred at room temperature overnight. The mixture was diluted with 100 mL of ether, and the solid was filtered from the mixture and dried thoroughly. The product was pure enough for further reactions. A sample was recrystallized from ethanol to give a pure product which melted with decomposition from 279°–292° C. Analysis: Calculated: C, 55.4; H, 5.6; N, 17.2. Found: C, 55.3; H, 5.5; N, 17.1.

EXAMPLE 11

2-Azidomethyl-1-(2-methylpropyl)-1H-imidazo[4,5-c]quinolin-4-amine

2-Chloromethyl-1(2-methylpropyl)-1H-imidazo[4,5-c]quinolin-4-amine hydrochloride (2.5 g; 0.0077 mol, Example 10) was suspended in N-methylpyrrolidone (15 mL). A solution of lithium azide (2.3 g) in water (45 mL) was added to the suspension. The resulting mixture was heated on the steam bath for 2 hr and then diluted with water (about 45 mL). The tan solid was washed with water and dried to yield 1.4 g (60.9%) of crude product. The solid was recrystallized from ethanol to give a pure product m.p. 174°–178° C. Analysis: C, 61.0; H, 5.8; N, 33.2. Found: C, 60.9; H, 5.6; N, 32.6.

EXAMPLE 12

1-(2-Methylpropyl)-2-morpholinomethyl-1H-imidazo[4,5-c]quinolin-4-amine

2-Chloromethyl-1-(2-methylpropyl)-1H-imidazo[4,5-c]quinolin-4-amine hydrochloride (Example 10, prepared from 2.0 g of the corresponding alcohol) was added to morpholine (5 mL). The mixture was refluxed for 4 hr. The resulting solution was cooled to room temperature. A solid precipitated. The solid was filtered from the mixture and slurried in aqueous sodium bicarbonate solution. The product was filtered from the mixture, washed with water, and dried to yield 1.7 g (68.0%) of solid, which was recrystallized from ethanol to give a pure product m.p. 228°–234° C. Analysis: Calculated: C, 67.2; H, 7.4; N, 20.6. Found: C, 67.3; H, 7.9; N, 20.6.

EXAMPLE 13

1-(2-Methylpropyl)-2-pyrrolidinomethyl-1H-imidazo[4,5-c]quinolin-4-amine

The pyrrolidinomethyl compound was prepared from 2-chloromethyl-1-(2-methylpropyl)-1H-imidazo[4,5-c]quinolin-4-amine hydrochloride (Example 10) by substituting pyrrolidine for morpholine in the method of Example 12. A crude yield of 1.90 g (63.3%) was obtained. Recrystallization of the crude solid from ethanol gave the pure product. m.p. 172°–187° C. Analysis: Calculated: C, 70.7; H, 7.8; N, 21.7. Found: C, 70.6; H, 7.8; N, 21.5.

EXAMPLE 14

4-Amino-1-(2-methylpropyl)-1H-imidazo[4,5-c]quinoline-2-methanamine

2-Azidomethyl-1(2-methylpropyl)-1H-imidazo[4,5-c]quinolin-4-amine (3.2 g, 0.0108 mol, Example 11) was added to ethanol (300 mL) and 5% Pd/C (about 1 g) was added to the mixture. The mixture was hydrogenated on a Parr apparatus until hydrogen uptake stopped. Hydrogen was removed and the mixture was flushed with hydrogen to regenerate the catalyst. Hydrogenation was resumed. This procedure was repeated until no more hydrogen was absorbed. The catalyst was filtered from the mixture and the filtrate was evaporated. The residue was recrystallized several times from ethanol to give yellowish crystals m.p. 287°–291° C. Analysis: Calculated: C, 66.9; H, 7.1; N, 26.0. Found: C, 66.5; H, 7.2; N, 25.1.

EXAMPLE 15

N-Acetyl-4-amino-1-(2-methylpropyl)-1H-imidazo[4,5-c]quinoline-2-methanamine 4-Amino-1-(2-methylpropyl)-1H-imidazo[4,5-c]quinoline-2-methanamine (1.1 g; 0.004 mol, Example 14) was added to acetic anhydride (3 mL). The mixture was stirred at room temperature for 5 hrs. The solution was then diluted with methanol (50 mL) and refluxed for 1 hr. The solution was concentrated and the residue made basic with aqueous sodium bicarbonate solution. The oily residue was extracted into dichloromethane. The extracts were dried over magnesium sulfate and evaporated to dryness. The residue was recrystallized from ethyl acetate to yield pure product m.p. 214°–218° C. Analysis: Calculated: C, 65.6; H, 6.8; N, 22.5. Found: C, 65.1; H, 6.6; N, 22.0.

EXAMPLE 16

α-Methyl-1-(2-methylpropyl)-1H-imidazo[4,5,-c]quinoline-2-methanol

3-Amino-4-(2-methylpropylamino) quinoline (29.0 g; 0.135 mol) and lactic acid (36 mL; 0.48 mol) were mixed and heated at 140° C. for 6 hr. The mixture was then dissolved in dilute hydrochloric acid and treated with charcoal. The solids were filtered from the mixture. The filtrate was made basic with ammonium hydroxide to precipitate the product as an oil. The oil was extracted into ethyl acetate. The ethyl acetate solution was treated with decolorizing carbon and the solids were filtered from the mixture. The filtrate was evaporated to dryness to yield a greenish oil which was pure enough for further reactions. A small sample was triturated with hexane to obtain a solid which was recrystallized from ethyl acetate for analysis. m.p. 152°–166° C. Analysis: Calculated: C, 71.4; H, 7.11; N, 15.6. Found: C, 71.1; H, 7.33; N, 15.4.

EXAMPLE 17

α-Methyl-1-(2-methylpropy)-1H-imidazo[4,5-c]quinoline-2-methyl Benzoate

α-Methyl-1-(2-methylpropyl)-1H-imidazo[4,5-c]quinoline-2-methanol (20.0 g; 0,074 mol, Example 16) was dissolved in dichloromethane (200 mL) and triethylamine (11.4 mL; 0.082 mol) was added to the solution. Benzoyl chloride (9.5 mL; 0,082 mol) was added dropwise to the stirred solution. The mixture was stirred at room temperature for 6 hr. The solution was washed with water and aqueous sodium bicarbonate solution, dried over magnesium sulfate and evaporated to yield 26.6 g of greenish, viscous oil. The product was pure enough for the following N-oxidation step but a small sample was purified by silica gel flash chromatography (ethyl acetate eluent) for analysis and characterization. m.p. 158°–163° C. Analysis: Calculated: C, 74.0; H, 6.2; N, 11.3. Found: C, 73.7; H, 6.2; N, 11.2.

EXAMPLE 18

α-Methyl-1-(2-methylpropyl)-1H-imidazo[4,5,c]quinoline-2-methyl Benzoate 5N Oxide α-Methyl-1-(2-methylpropyl)-1H-imidazo[4,5-c]quinoline-2-methyl benzoate (11.7 g; 0.031 mol, Example 17) was added to ethanol and 32% peracetic acid (11.1 mL; 0.0092 mol) was added to the solution. The mixture was heated at 65° C. for 5 hr. The solution was then evaporated to dryness. The residue was treated with aqueous sodium bicarbonate solution. The product was extracted into ethyl acetate, dried over magnesium sulfate, and evaporated to yield an oily residue containing a trace of starting material. The crude product was used in subsequent reactions.

EXAMPLE 19

4-Chloro-α-methyl-1-(2-methylproyl)-1H-imidazo[4,5-c]quinoline-2-methyl Benzoate α-Methyl-1-(2-methylpropyl)-1H-imidazo[4,5-c]quinoline-2-methyl benzoate 5N oxide (9.2 g; 0.0236 mol, Example 18) was added to dichloromethane (200 mL). Phosphorous oxychloride (2.6 mL; 0.0283 mol) was added to the solution. The reaction mixture was stirred at room temperature for 2½ hr. The solution was evaporated and the residue was mixed with water and ammonium hydroxide. The oil was extracted into ethyl acetate. The extracts were dried over magnesium sulfate and evaporated to dryness. A yield of 7.6 g (79.2%) of product was obtained as a glassy solid, which was used as such for the next reaction.

EXAMPLE 20

4-Amino-α-methyl-1-(2-methylpropyl)-1H-imidazo[4,5-c]quinoline-2-methanol

4-Chloro-α-methyl-1-(2-methylpropyl)-1H-imidazo[4,5-c]quinoline-2-methyl benzoate (3.7 g; 0.009 mol, Example 19) was added to 15% methanolic ammonia (50 mL). The mixture was heated in a Parr bomb at 165° C. for 6 hr. The resulting reaction mixture was evaporated and the residue was slurried in aqueous sodium bicarbonate. The product was extracted into dichloromethane, and the extracts were washed with aqueous sodium bicarbonate and dried over magnesium sulfate. The organic extracts were evaporated to dryness to yield an oily solid. The solid was purified by silica gel column chromatography to yield two products, the intended product and the 4-(N-methyl) derivative. The intended product ($R_f$=0.36 silica gel TLC, ethyl acetate eluent) was recrystallized from ethanol to yield a solid m.p. 190°–195° C. Analysis: Calculated: C, 67.6; H, 7.1; N, 19.7. Found: C, 67.6; H, 7.1; N, 19.7. The 4-(N-methyl) derivative was recrystallized from ethyl acetate to give a solid, m.p. 145°–149° C. Analysis: Calculated: C, 68.4; H, 7.4; N, 18.8. Found: C, 68.3; H, 7.4; N, 18.7.

EXAMPLE 21

α,α-Dimethyl-1-(2-methylpropyl)-1H-imidazo[4,5-c]quinoline-2-methanol

3-Amino-4-(2-methylpropyl amino) quinoline (28.7 g; 0.133 mol) and 2-hydroxyisobutyric acid (27.8 g; 0.267 mol) were mixed and the mixture was heated at 160° C. for 5 hrs. Water was added to the dark mixture and a green oil formed. The oil was extracted with ether to yield 8.6 g of an oil which contained two products. The mixture was purified by silica gel column chromatography to yield 3.2 g of the intended product. A small amount was recrystallized from ethyl acetate for analysis and characterization. m.p. 156°–164° C. Analysis: Calculated: C, 72.1; H, 7.5; N, 14.8. Found: C, 71.9; H, 7.4; N, 14.6.

EXAMPLE 22

4-Chloro-α,α-dimethyl-1-2-methylpropyl)-1H-imidazo[4,5-c]quinoline-2-methanol

α,α-Dimethyl-1-(2-methylpropyl)-1H-imidazo[4,5-c]quinoline-2-methanol (3.0 g; 0.0106 mol, Example 21) was dissolved in ethanol (30 mL) and 32% peracetic acid (3.8 mL; 0.0108 mol) was added. The mixture was heated at 65° C. for 4 hr. The solution was concentrated and the residue was slurried in aqueous sodium bicarbonate solution. The oily product was extracted into ethyl acetate. The extracts were dried over magnesium sulfate and evaporated to dryness. A yield of 2.8 g of N oxide as a yellow solid was obtained. The intermediate N oxide was added to dichloromethane and 1.1 eq of phosphorous oxychloride was added to the vigorously stirred mixture. The mixture was stirred at room temperature overnight and then concentrated. The residue was slurried in aqueous sodium bicarbonate and extracted into ethyl acetate. The product was purified by silica gel flash chromatography (10% ethyl acetate in dichloromethane). A small amount was recrystallized from ethyl acetate to give a solid, m.p. 205°–210° C. Analysis: C, 64.2; H, 6.3; N, 13.2. Found: C, 64.2; H, 6.3; N, 13.1.

EXAMPLE 23

4-Amino-α,α-dimethyl-1-(2-methylpropyl)-1H-imidazo[4,5-c]quinoline-2-methanol

4-Chloro-α,α-dimethyl-1-(2-methylpropyl)-1H-imidazo-[4,5-c]quinoline-2-methanol (Example 22) was aminated in a Parr bomb at 150° C. using 15% methanolic ammonia. The product was purified by silica gel column chromatography (5% methanol in ethyl acetate as eluent). The product was then recrystallized from ethyl acetate/hexane to give a solid, m.p. 214°–217° C. Analysis: Calculated: C, 68.4; H, 7.4; N, 18.8. Found: C, 68.2; H, 7.4; N, 18.7.

EXAMPLE 24

1-Phenylmethyl-1H-imidazo[4,5-c]quinoline-2-methanol 3-amino-4-(benzylamino) quinoline (9.5 g; 0.038 mol) and glycolic acid (6.8 g; 0.089 mol) were mixed and the mixture was heated at 150° C. for about 4 hr. The dark mixture was then dissolved in dilute hydrochloric acid with heating. Upon cooling a precipitate formed and was filtered from the mixture. The solid was dissolved in hot water. The solution was then made basic with ammonium hydroxide to precipitate the product. A second, less pure, small crop was obtained from the original filtrate by making it basic with ammonium hydroxide. The solid was triturated in ethyl acetate to give a green colored powder. Total yield was 82%. The product was recrystallized from methanol to give a pure sample m.p. 211°–213° C. Analysis: Calculated: C, 74.7; H, 5.2; N, 14.5. Found: C, 74.4; H, 5.1; N, 14.4.

EXAMPLE 25

1-Phenylmethyl-1H-imidazo[4,5-c]quinoline-2-methyl Acetate

1-Phenylmethyl-1H-imidazo[4,5-c]quinoline-2-methanol (7.5 g; 0.026 mol, Example 24) was added to dichloromethane (70 mL). Acetic anhydride (5.7 mL) and pyridine (3.1 mL) were added to the mixture. The mixture was refluxed for about 6 hr and the solids were then filtered from the mixture. The filtrate was evaporated and the residue was filtered, slurried consecutively in water and methanol/water. The solid was then filtered from the mixture and dried to yield 6.7 g (74.4%) of product. The solid was recrystallized from methanol. m.p. 216°–218° C. Analysis: C, 72.5; H, 5.2; N, 12.7. Found: C, 72.1; H, 5.1; N, 12.6.

EXAMPLE 26

1-Phenylmethyl-1H-imidazo[4,5-c]quinoline-2-methyl Acetate 5N Oxide

1-Phenylmethyl-1H-imidazo[4,5-c]quinoline-2-methyl acetate (6.7 g; 0.019 mol, Example 25) and 32% peracetic acid (4.6 mL; 0.0214 mol) were added to a mixture of ethyl acetate (125 mL) and ethanol (250 mL). The mixture was refluxed for 6 hr. The solution was evaporated to dryness and the residue was slurried with aqueous sodium bicarbonate solution. The solid was filtered from the mixture, washed with water, and dried to yield 7.2 g of crude product. The crude product was recrystallized from ethyl acetate. m.p. 229°–232° C. Analysis: Calculated: C, 69.2; H, 4.9; N, 12.1. Found: C, 69.1; H, 4.9; N, 12.0.

EXAMPLE 27

4-Amino-1-phenylmethyl-1H-imidazo[4,5-c]quinoline-2-methanol

1-Phenylmethyl-1H-imidazo[4,5-c]quinoline-2-methyl acetate 5N oxide (5.6 g; 0.0162 mol, Example 26) was suspended in a mixture of dichloromethane (150 mL,) and ammonium hydroxide (55 mL). The mixture was cooled to 0°–5° C. A solution of p-toluenesulfonyl chloride (3.4 g; 0.0178 mol) in dichloromethane (25 mL) was added dropwise to the vigorously stirred mixture while maintaining the temperature at 0°–5° C. When the addition was complete the mixture was allowed to stir at room temperature overnight. The dichloromethane was then evaporated from the mixture and the solid was filtered from the mixture. The tan solid was washed with water and dried to yield 5.5 g of product which was found to be the acetate of the intended product. The acetate was added to a mixture of methanol (300 mL) and dichloromethane (100 mL). The mixture was made basic with 25% methanolic sodium methoxide. After about ½ hr the product began to precipitate from solution. The solid was filtered from the mixture, washed sequentially with water and methanol, and dried to yield 3.1 g (64.6%). A sample was recrystallized from methanol/dichloromethane. m.p. >300° C. Analysis: Calculated: C, 71.0; H, 5.3; N, 18.4. Found: C, 71.1, H, 5.0; N, 18.1.

EXAMPLE 28

2-Chloromethyl-1-phenylmethyl-1H-imidazo[4,5-c]quinolin-4-amine Hydrochloride

4-Amino-1-phenylmethyl-1H-imidazo[4,5-c]quinoline-2-methanol (2.0 g; 0.0066 mol, Example 27 was added in small portions to thionyl chloride (10 mL). After stirring at room temperature for 30 min the product had crystallized from solution. The mixture was diluted with dry ether (75 mL). The solid was filtered from the mixture, washed with ether, and thoroughly dried. The product was used as such without further characterization or purification.

EXAMPLE 29

2-Morpholinomethyl-1-phenylmethyl-1H-imidazo[4,5-c]quinolin-4-amine

2-Chloromethyl-1-phenylmethyl-1H-imidazo[4,5-c]quinolin-4-amine hydrochloride (Example 28, prepared from 2.0 g of the alcohol) was added to morpholine (5.0 mL) and the mixture was refluxed for 4 hr. The mixture was then cooled to room temperature and the solid was filtered from the mixture. The solid was slurried in aqueous sodium bicarbonate solution, filtered from the mixture, and dried. A crude yield of 2.0 g of product as a white solid was obtained. The crude product was recrystallized from methanol/dichloromethane. m.p. >300° C. Analysis: Calculated: C, 70.7; H, 6.2; N, 18.8. Found: C, 70.4; H, 6.2; N, 18.6.

EXAMPLE 30

4-Amino-N-hydroxyethyl-N-methyl-1-phenylmethyl-1H-imidazo[4,5,c]quinoline-2-methanamine Hemihydrate 2-Chloromethyl-1-phenylmethyl-1H-imidazo[4,5-c]quinolin-4-amine hydrochloride (Example 28, prepared from 1.4 g of the alcohol) was added to N-methylethanolamine (20 mL). The mixture was heated in an oil bath for 3 hr at about 130° C. The solution was diluted with water and the mixture extracted with diethyl ether (7×200 mL). The combined extracts were washed with saturated sodium chloride solution and evaporated to dryness to yield an orange solid. The crude product was recrystallized from methanol/dichloromethane. m.p. 188°–195° C. Analysis: Calculated: C, 68.1; H, 6.5; N, 18.9. Found: C, 68.4; H, 6.5: N, 18.7.

EXAMPLE 31

2-Methylthiomethyl-1-phenylmethyl-1H-imidazo[4,5-c]quinolin-4-amine

2-Chloromethyl-1-phenylmethyl-1H-imidazo[4,5-c]quinolin-4-amine hydrochloride (Example 28, prepared from 2.11 g of the alcohol) was added to a solution of methanethiol (1.33 g; 0.028 mol) and sodium methoxide (1.5 g; 0.028 mol) in methanol. The solid dissolved upon addition and a cream colored solid precipitated during addition. After stirring at room temperature for several hours the mixture was diluted with water. The solid was filtered from the mixture, washed with water, and dried. A crude yield of 2.3 g was obtained. The product was purified by silica gel flash chromatography (10% methanol in ethyl acetate eluent) and recrystallized from methanol/dichloromethane to give a cream colored solid, m.p. 217°–219° C. Analysis: Calculated: C, 68.2; H, 5.4; N, 16.8. Found: C, 67.5; H, 5.3; N, 16.6.

EXAMPLE 32

2-Methoxymethyl-1-(2-methylpropyl)-1H-imidazo[4,5-c]quinoline

3-Amino-4-(2-methylpropylamino)quinoline (5.0 g; 0.023 mol) and methoxyacetic acid (20 mL) were mixed and heated at about 200° C. until all bubbling had stopped. Heating was continued for 5–10 min longer and the dark solution was allowed to cool to room temperature. The solution was diluted with water, made strongly basic with 50% sodium hydroxide and extracted with ether. The combined extracts were dried over magnesium sulfate and evaporated to dryness to yield 5.2 g of crude product. The crude product was used as such for further reactions. A small sample was recrystallized from ether to yield nearly colorless crystals, m.p. 96°–99° C. Analysis: Calculated: C, 71.4; H, 7.1; N, 15.6. Found: C, 71.1; H, 7.0; N, 15.6.

EXAMPLE 33

2-Methoxymethyl-1-(2-methylpropyl)-1H-imidazo[4,5-c]quinoline 5N Oxide Monohydrate 2-Methoxymethyl-1-(2-methylpropyl)-1H-imidazo[4,5-c]quinoline (5.0 g; 0.0186 mol, Example 32) was added to ethyl acetate (100 mL) containing 32% peracetic acid (4.9 g; 0.0206 mol). The solution was refluxed for about 15 min. The solution was then evaporated. The residue was slurried in aqueous sodium bicarbonate and the solid was filtered from the mixture. A second crop was obtained by allowing the filtrate to stand overnight at room temperature. A combined yield of 4.6 g (86.8%) of crude product was obtained. A pure sample was obtained by recrystallized from isopropyl alcohol. m.p. broad; Analysis: Calculated: C, 63.5; H, 7.0; N, 13.8. Found: C, 63.5; H, 6.7; N, 13.8.

EXAMPLE 34

2-Methoxymethyl-1-(2-methylpropyl)-1H-imidazo[4,5-c]quinolin-4-amine

2-Methoxymethyl-1-(2-methylpropyl)-1H-imidazo[4,5-c]quinoline 5N oxide (4.0 g; 0.014 mol, Example 33) was dissolved in dichloromethane (80 mL). Concentrated ammonium hydroxide (30 mL) was added to the solution. The mixture was cooled to 0°–5° C. and vigorously stirred as a solution of p-toluenesulfonyl chloride (2.9 g; 0.015 mol) in dichloromethane (15 was added dropwise. The temperature was maintained at 0°–5° C. during addition. When addition was complete the mixture was stirred at room temperature for 1 hr. The dichloromethane was separated from the aqueous layer, dried over magnesium sulfate, and evaporated to dryness to yield 1.7 g of a tan powder. Two recrystallizations from isopropyl alcohol gave an analytically pure sample, m.p. 157°–160° C. which analyzes for a quarter mole of water. Analysis: Calculated: C, 66.5; H, 7.2; N, 19.4. Found: C, 66.9; H, 6.9; N, 19.0.

EXAMPLE 35

1-(2-Methoxyethyl)-2-methoxymethyl-1H-imidazo[4,5-c]quinoline 4-(2-Methoxyethylamino)-3-nitroquinoline (16.24 g; 0.066 mol) was added to a mixture of ethyl acetate (1500 mL), 5% platinum on carbon (1 g), and magnesium sulfate (6 g). The mixture was hydrogenated on a Parr apparatus at 30 psi initial pressure. When the hydrogenation was complete, the solids were filtered off and the ethyl acetate was evaporated. The resulting diamine intermediate was heated with methoxyacetic acid (70 mL) at 150° C. for 2–3 hours and then at 120° C. for 2–3 hours. The reaction mixture was poured into water (400 mL), made strongly basic with 6N sodium hydroxide and then extracted with ether (3×200 mL). The ether extracts were combined, washed with brine then evaporated to provide 9.9 g of an oil which crystallized on standing. The aqueous layers were extracted again with ether (4×200 mL). The extracts were combined, washed with brine and evaporated. The residue was recrystallized from ethyl acetate to provide 1.5 g yellow needles. Analysis: Calculated: C, 66.4; H, 6.3; N, 15.5; Found: C, 66.6; H, 6.4; N, 16.1.

EXAMPLE 36

1-(2-Methoxyethyl)-2-methoxymethyl-1H-imidazo[4,5-c]quinoline 5N Oxide 1-(2-Methoxyethyl)-2-methoxymethyl-1H-imidazo[4,5-c]quinoline (13.3 g, 0.044 mol, Example 35) was dissolved in warm ethyl acetate (150 mL) and 32% peracetic acid (12.0 mL) was slowly added to the solution. The mixture was heated at reflux for 2–3 hours and then allowed to stand at room temperature overnight. The resulting precipitate was collected, rinsed with ethyl acetate then coevaporated with toluene to yield 2.6 g of a solid. The ethyl acetate filtrate was evaporated. The resulting residue was taken up in about 300 mL of water and made basic with concentrated ammonium hydroxide. The resulting precipitate was collected, rinsed with water, coevaporated with toluene and dried to provide 5.6 g of solid. A total crude yield of 8.2 g was obtained and the material was used in subsequent reactions.

EXAMPLE 37

1-(2-Methoxyethyl)-2-methoxymethyl-1H-imidazo[4,5-c]quinolin-4-amine 1-(2-Methoxyethyl)-2-methoxymethyl-1H-imidazo[4,5-c]quinoline 5N oxide (7.67 g; 0.027 mol, Example 36) was dissolved in methylene chloride (100 mL) and cooled to 0°–5° C. Cold concentrated ammonium hydroxide (75 mL) was added with stirring and continued cooling and a precipitate formed. A solution of p-toluenesulfonyl chloride (5.59 g; 0.029 mol) in methylene chloride (20 mL) was slowly added with continued stirring and cooling. The mixture was maintained at 0°–5° C. for about 30 minutes after the addition and then stirred at room temperature overnight. The methylene chloride was evaporated from the mixture and the solid was filtered from the mixture. The volume of the aqueous filtrate was reduced under a stream of nitrogen and the resulting precipitate was collected, rinsed with water and dried to provide 5.1 g of a solid. The solid was taken up in water, acidified with concentrated hydrochloric acid then filtered. The filtrate was made basic with 6N sodium hydroxide. The resulting precipitate was collected, rinsed with water and dried to provide colorless needles, m.p. 126°–127° C. Analysis: Calculated: C, 62.9; H, 6.3; N, 19.6; Found: C, 62.9; H, 6.05: N, 19.3.

EXAMPLE 38

2-Ethoxymethyl-1-(2-methylpropyl)-1H-imidazo-4,5-c]guinoline 4-(2-Methylpropylamino)-3-nitroguinoline (30.5 g; 0.12 mol) was added to a mixture of ethyl acetate (800 mL), 5% platinum on carbon (1.5 g) and magnesium sulfate (10 g).

The mixture was hydrogenated on a Parr apparatus at an initial hydrogen pressure of 30 psi. When the hydrogenation was complete, the solids were removed and the ethyl acetate was evaporated. The resulting intermediate diamine was mixed with ethoxyacetic acid (80.5 mL) and heated with stirring at 130° C. for 2–3 hours. The reaction mixture was cooled, poured into 400 mL of water and then made basic with 6N sodium hydroxide. A green solid was collected and dried to provide 8.8 g of the desired product. The structure was confirmed by nuclear magnetic resonance spectroscopy. The liltrate was extracted with ether (4×150 mL). The ether extracts were combined then evaporated to provide 11.2 g of a green solid. The solids were combined and used in subsequent reactions.

EXAMPLE 39

2-Ethoxymethyl-1-(2-methylpropyl)-1H-imidazo[4,5-c]quinoline 5N Oxide

2-Ethoxymethyl-1-(2-methylpropyl)-1H-imidazo[4,5-c]quinoline (17.4 g; 0.061 mol, Example 38) was dissolved in warm ethyl acetate (150 mL) and 32% peracetic acid (14.5 mL) was slowly added to the solution. The mixture was refluxed for 2–3 hours and then cooled to room temperature. The precipitate was collected, rinsed with a small amount of ethyl acetate and dried to provide 6.3 g of white solid. The structure was confirmed by nuclear magnetic resonance spectroscopy. This material was used in subsequent reactions.

EXAMPLE 40

2-Ethoxymethyl-1-(2-methylpropyl)-1H-imidazo[4,5-C]quinolin-4-amine

2-Ethoxymethy-1-(2-methylpropyl)-1H-imidazo[4,5-c]quinoline 5N oxide (6.0 g; 0.02 mol, Example 39) was suspended in methylene chloride (150 mL) and cooled to 0°–5° C. Concentrated ammonium hydroxide (60 mL) was cooled to 0°–5° C. and added to the suspension. A solution of p-toluenesulfonyl chloride (4.2 g; 0.022 mol) in methylene chloride (20 mL) was slowly added to the mixture with stirring. The mixture was allowed to stir at room temperature overnight. The methylene chloride was evaporated and the resulting precipitate was collected and rinsed with water to give 6.3 g of crude material. The crude material was triturated with ether. The solid was collected, rinsed with ether and dried to give an analytically pure sample, m.p. 133°–137° C. that analyzed for half a mole of water. Analysis: Calculated: C, 66.5; H, 7.4; N, 18.2; Found: C, 67.0; H, 7.3; N, 18.2.

EXAMPLE 41

4-(3-Methoxypropylamino)-3-nitroquinoline

4-Hydroxy-3-nitroquinoline (19.0 g, 0.10 mol) was suspended in methylene chloride (250 mL). Thionyl chloride (8.0 mL, 0.11 mol) was combined with dimethylformamide (8.5 mL, 0.11 mol) and slowly added to the suspension. The resulting mixture was stirred and heated at reflux for about 2 hours. 3-Methoxypropylamine (10.25 g, 0.115 mol) was combined with triethylamine (15 mL, 0.20 mol) and slowly added to the mixture with stirring. A vigorous heat of reaction was observed. The mixture was evaporated and the residue was suspended in water. The suspension was acidified with concentrated hydrochloric acid. A dark solid was collected. The filtrate was made basic with concentrated ammonium hydroxide. The precipitate was collected, rinsed with water, and dried to provide 8.4 g of a yellow solid, m.p. 93°–95° C. The dark solid was suspended in 2 liters of water, acidified with concentrated hydrochloric acid, heated on a steam bath for 2–3 hours and then filtered while still hot. The filtrate was made basic with concentrated ammonium hydroxide. The precipitate was collected, rinsed with water, and dried to provide 9.2 g of a yellow solid, m.p. 93°–95° C. Analysis: Calculated: C, 59.8; H, 5.8; N, 16.1; Found: C, 59.6; H, 5.7; N, 16.0.

EXAMPLE 42

2-Ethoxymethyl-1-(3-methoxypropyl)-1H-imidazo[4,5-c]quinoline 4-(3-methoxypropylamino)-3-nitroquinoline (14.6 g; 0.056 mol, Example 41) was added to a mixture of ethyl acetate (1300 mL), 5% platinum on carbon (1.0 g), and magnesium sulfate (5.0 g). The mixture was hydrogenated on a Parr apparatus at an initial hydrogen pressure of 30 psi. When the hydrogenation was complete, the solids were removed and the ethyl acetate was evaporated. The residual intermediate diamine was mixed with ethoxyacetic acid (60 mL) and heated at 120° C. for about 8 hours. The reaction mixture was cooled to room temperature, poured into water, made basic with 6N sodium hydroxide and then extracted with ether (5×100 mL). The ether extracts were combined, dried with magnesium sulfate, then evaporated. The residue was purified by silica gel chromatography (20% methanol in ethyl acetate as eluent) to give 13.3 g of a green oil. This material was used in subsequent reactions.

EXAMPLE 43

2-Ethoxymethyl-1-(3-methoxypropyl-1H-imidazo[4,5-c]quinoline 5N Oxide

2-Ethoxymethyl-1-(3-methoxypropyl)-1H-imidazo[4,5-c]quinoline (13.3 g; 0.044 mol, Example 42) was dissolved in ethyl acetate (150 mL) and 32% peracetic acid (12 mL) was slowly added to the solution. The reaction mixture was heated at reflux for 3–4 hours then cooled to room temperature. The mixture was evaporated. The residue was diluted with water (300 mL), made basic with concentrated ammonium hydroxide, then extracted with ether (7×100 mL). The ether extracts were combined, dried with magnesium sulfate and evaporated to provide a small amount of a yellow oil. The aqueous base layer was then extracted with ethyl acetate (6×100 mL). The ethyl acetate extracts were combined, washed with brine, dried over magnesium sulfate and evaporated to provide a yellow solid. The solid was coevaporated with toluene to provide 3.56 g of a yellow crystalline solid. The structure was confirmed by nuclear magnetic resonance spectroscopy. The material was used in subsequent reactions.

EXAMPLE 44

2-Ethoxymethyl-1-(3-methoxypropyl)-1H-imidazo[4,5-c]quinolin-4-amine

2-Ethoxymethyl-1-(3-methoxypropyl)-1H-imidazo[4,5-c]quinolin-4-amine 5N oxide (3.5 g; 0.011 mol, Example 43) was dissolved in methylene chloride (25 mL) and cooled to 0°–5° C. Concentrated ammonium hydroxide (35 mL) was cooled to 0°–5° C. then added to the solution. The resulting mixture was stirred for about 15 minutes. A solution of p-toluenesulfonyl chloride (2.33 g; 0.012 mol) in methylene chloride (10 mL) was slowly added with stirring. The reaction mixture was stirred at 0°–5° C. for an additional 30 minutes and then at room temperature overnight. The methylene chloride was evaporated. The resulting precipitate was collected, rinsed with water then recrystallized first from ethyl acetate and then from dichloroethane to give a crystalline solid, m.p. 123.5°–125° C. Analysis: Calculated: C, 64.95; H, 7.05: N, 17.8; Found: C, 65.0; H, 7.0; N, 17.7.

EXAMPLE 45

1-(2-Methylpropyl)-α-phenyl-1H-imidazo[4,5-c]quinoline-2-methanol

3-Amino-4-(2-methylpropylamino) quinoline (43.5 g; 0.20 mol) and formic acid (300 mL) were combined and heated on a steam bath for several hours. The reaction mixture was concentrated under vacuum, diluted with water, basified with ammonium hydroxide then extracted twice with ether. The ether extracts were treated with activated charcoal then combined for a total volume of 1200 mL. The volume was reduced to 500 mL, cooled, then filtered to provide 31.1 g of a light green crystalline solid 1-(2-methylpropyl)-1H-imidazo[4,5-c]quinoline.

1-(2-Methylpropyl)-1H-imidazo[4,5-c]quinoline (4 g; 0.017 mol) was dissolved in tetrahydrofuran (50 mL) then cooled to −78° C. A 7.75 mL portion of n-butyl lithium (2.5M in hexanes) was added dropwise to the cooled solution. At 15 minutes post addition, benzaldehyde (2.7 mL; 0.027 mol) was added and the reaction mixture was allowed to warm slightly. The reaction was quenched with water then diluted with ethyl ether. The ether was separated, dried with magnesium sulfate then concentrated under vacuum. The resulting residue was purified by silica gel chromatography using 5% methanol in methylene chloride as the eluent to give an oily yellow solid. This material was recrystallized from methylene chloride/hexane to provide a white crystalline solid, m.p. 160°–166° C. Analysis: Calculated: C, 76.1; H, 6.4; N, 12.7; Found: C, 75.9; H, 6.3; N, 12.7.

EXAMPLE 46

1-(2-Methylpropyl)-α-phenyl-1H-imidazo[4,5-c]quinoline-2-methyl Acetate 1-(2-Methylpropyl)-α-phenyl-1H-imidazo[4,5-c]quinoline-2-methanol (3 g; 9 mmol, Example 45) was dissolved in methylene chloride (50 mL) then combined with acetic anhydride (1.3 mL; 13.5 mmol) and triethylamine (1.6 mL; 11.8 mol) and stirred at room temperature overnight. The reaction mixture was diluted with methylene chloride, washed sequentially with water and saturated sodium bicarbonate solution, dried over magnesium sulfate and concentrated under vacuum. The resulting residue was purified by silica gel flash chromatography (50% ethyl acetate in methylene chloride as eluent) to provide a white solid. The structure was confirmed by nuclear magnetic resonance spectroscopy.

EXAMPLE 47

2-(α-Acetoxybenzyl)-1-(2-methylpropyl)-1H-imidazo[4,5-c]quinoline 5N Oxide 1-(2-Methylpropyl)-α-phenyl-1H-imidazo[4,5-c]quinoline-2-methyl acetate (3 g; 8 mmol, Example 46) was dissolved in ethyl acetate (50 mL) then combined with peracetic acid (2.2 g; 8.8 mmol) and heated at reflux for about an hour. The reaction mixture was allowed to cool and then was stirred at room temperature for several days. The resulting precipitate was collected, rinsed with ethyl acetate and dried to provide 2.6 g of a solid. The structure was confirmed by nuclear magnetic resonance spectroscopy.

EXAMPLE 48

4-Amino-1-(2-methylpropyl)-α-phenyl-1H-imidazo[4,5-c]quinoline-2-methanol 2-(α-acetoxybenzyl)-1-(2-methylpropyl)-1H-imidazo[4,5-c]quinoline 5N oxide (2.6 g; 6.7 mmol, Example 47) was dissolved in methylene chloride (40 mL), combined with benzoyl isocyanate (1.2 g; 7.3 mmol) and heated at reflux for about one hour. The reaction mixture was diluted with methylene chloride, washed with water, dried over magnesium sulfate and concentrated under vacuum. The residue was taken up in methanol, combined with a catalytic amount of 25% sodium methoxide in methanol, and heated at reflux for several hours. The reaction product was purified by silica gel chromatography using 2–5% methanol in methylene chloride then recrystallized from ethyl acetate-hexane. The recrystallized material was co-evaporated twice with methylene chloride to provide about 0.5 g of a solid, m.p. 125°–140° C. Analysis: Calculated: C, 72.8; H, 6.4; N, 16.2; Found: C, 71.9; H, 5.6; N, 15.6. Mass spectrum m/z=347.

EXAMPLE 49

2-(α-Methoxybenzyl)-1-(2-methylpropyl)-1H-imidazo[4,5-c]quinoline 1-(2-Methylpropyl)-α-phenyl-1H-imidazo[4,5-c]quinoline-2-methanol (5.0 g; 15 mmol, Example 45) was dissolved in N,N-dimethylformamide (25 mL) then added to a cooled (0°–5° C.) suspension of sodium hydride (0.5 g; 16.6 mmol) in N,N-dimethylformamide (100 mL). The reaction mixture was stirred at room temperature for about one hour then combined with methyl iodide (1.4 mL; 22.6 mmol). Stirring was continued until the reaction was complete as indicated by thin layer chromatography. The reaction mixture was diluted with ether then quenched with water. The ether layer was separated, washed twice with water, dried over magnesium sulfate then evaporated under vacuum. The residue was triturated with methylene chloride/hexane to provide 4.5 g of a solid. The structure was confirmed by nuclear magnetic resonance spectroscopy.

EXAMPLE 50

2-(α-Methoxybenzyl)-1-(2-methylpropyl)-1H-imidazo[4,5-c]quinoline 5N oxide 2-(α-Methoxybenzyl)-1-(2-methylpropyl)-1H-imidazo[4,5-c]quinoline (4.5 g; 13 mmol, Example 49) was dissolved in ethyl acetate (70 mL), combined with peracetic acid (3.4 g; 14 mmol) and heated at reflux for several hours. The reaction mixture was diluted with ethyl acetate, washed with water, dried over magnesium sulfate and concentrated under vacuum. The residue was purified by silica gel chromatography (1–5% methanol in methylene chloride as eluent) to give 3.9 g of an oil which solidified on standing. The structure was confirmed by nuclear magnetic resonance spectroscopy.

EXAMPLE 51

2-(α-Methoxybenzyl)-1-(2-methylpropyl)-
1H-imidazo[4,5-c]quinolin-4-amine 2-(α-Methoxybenzyl)-1-(2-methylpropyl)-1H-imidazo[4,5-c]quinoline 5N oxide (3.9 g; 10.8 mmol, Example 50) was dissolved in methylene chloride (60 mL) then mixed with ammonium hydroxide (20 mL). The mixture was cooled in an ice bath while a solution of p-toluenesulfonyl chloride (2.2 g; 11.8 mmol) in methylene chloride (20 mL) was added. The reaction mixture was allowed to warm to room temperature and then was stirred for several hours. The organic phase was separated, washed with water, dried over magnesium sulfate and concentrated under vacuum. The residue was recrystallized from ethyl acetate/hexane to provide 2.5 g of a solid, m.p. 183°–184° C. Analysis: Calculated: C, 73.3; H, 6.7; N, 15.5; Found: C, 73.1; H, 6.7; N, 15.3.

EXAMPLE 52

α-(4-Chlorophenyl)-1-(2-methylpropyl)-
1H-imidazo[4,5-c]quinoline-2-methanol

Using the method of Example 45, 1-(2-methylpropyl)-1H-imidazo[4,5-c]quinoline (2.5 g) was reacted with 4-chlorobenzaldehyde to provide 3.1 g of a yellow solid. The structure was confirmed by nuclear magnetic resonance spectroscopy.

EXAMPLE 53

α-(4-Chlorophenyl)-1-(2-methylpropyl)-
1H-imidazo[4,5-c]quinoline-2-methyl Acetate Using the method of Example 46, α-(4-chlorophenyl-1-(2-methylpropyl)-1H-imidazo[4,5-c]quinoline-2-methanol (2.6 g, 7.1 mmol, Example 52) was reacted with acetic anhydride to provide the desired product as a thick oil. The structure was confirmed by nuclear magnetic resonance spectroscopy.

EXAMPLE 54

2-(α-Acetoxy-4-chlorobenzyl)-1-(2-methylpropyl)-
1H-imidazo[4,5-c]quinoline 5N Oxide Using the method of Example 47, α-(4-chlorophenyl)-1-(2-methylpropyl)-1H-imidazo[4,5-c]quinoline-2-methyl acetate (2.9 g, 7.1 mmol, Example 53) was oxidized with peracetic acid to provide the 5N oxide as an oil.

EXAMPLE 55

4-Amino-α-4-chlorophenyl)-1-(2-methylpropyl)-
1H-imidazo[4,5-c]quinoline-2-methanol Using the method of Example 48, 2-(α-acetoxy-4-chlorobenzyl)-1-(2-methylpropyl)-1H-imidazo[4,5-c]quinoline 5N oxide (3.3 g, 7.8 mmol, Example 54) was reacted with benzoyl isocyanate and hydrolyzed to provide 0.8 g of the desired product as solid, m.p. 140°–145° C. Analysis: Calculated: C, 66.2; H, 5.6; N, 14.7; Found: C, 65.6; H, 5.5; N, 14.4.

EXAMPLE 56

α-Butyl-1-(2-methylpropyl)-1H-imidazo[4,5-c]quinoline-2-methanol

Using the method of Example 45, 1-(2-methylpropyl)-1H-imidazo[4,5-c]quinoline (20 g; 89 mmol) was reacted with valeraldehyde to provide 11.6 g of the desired product as a solid.

EXAMPLE 57

2-(1-Acetoxypentyl)-1-(2-methylpropyl)-
1H-imidazo[4,5-c]quinoline

Using the general method of Example 46, α-butyl-1-(2-methylpropyl)-1H-imidazo[4,5-c]quinoline-2-methanol (11.6 g; 37 mmol, Example 56) was reacted with acetic anhydride to provide the desired product.

EXAMPLE 58

2-(1-Acetoxypentyl)-1-(2-methylpropyl)-
1H-imidazo[4,5-c]quinoline 5N Oxide

Using the general method of Example 47, 2-(1-acetoxypentyl)-1-(2-methylpropyl)-1H-imidazo[4,5-c]quinoline (11.5 g; 32 mmol, Example 57) was oxidized with peracetic acid to provide the desired 5N oxide.

EXAMPLE 59

2-fl-Acetoxypentyl)-1-(2-methylpropyl)-
1H-imidazo[4,5-c]quinolin-4-amine

Using the general method of Example 51, 2-(1-acetoxypentyl)-1-(2-methylpropyl)-1H-imidazo[4,5-c]quinoline 5N oxide (12 g; 32 mmol, Example 58) was reacted with tosyl chloride and ammonium hydroxide to provide the desired amine.

EXAMPLE 60

4-Amino-α-butyl-1-(2-methylpropyl)-
1H-imidazo[4,5-c]quinoline-2-methanol
Hemihydrate Several drops of 25% sodium methoxide in methanol were added to a solution of 2-(1-acetoxypentyl)-1-(2-methylpropyl)-1H-imidazo[4,5-c]quinolin-4-amine (12 g; 32 mmol, Example 59) in methanol and the resulting mixture was heated at reflux for about one hour. The reaction was concentrated under vacuum to provide a solid. A portion of this solid was taken up in a large volume of methylene chloride, washed with water, dried over magnesium sulfate and reduced to a volume of about 50 mL. The resulting precipitate was collected and dried to provide 2.6 g of a white crystalline solid, m.p. 208°–211° C. Analysis: Calculated: C, 68.0; H, 8.1; N, 16.7; Found: C, 67.8; H, 7.7; N, 16.6.

EXAMPLE 61

2-(1-Methoxypentyl)-1-(2-methylpropyl)-
1H-imidazo[4,5-c]quinolin-4-amine

Sodium hydride (0.32 g; 10.1 mmol) was added to a suspension of 4-amino-α-butyl-1-(2-methylpropyl)-1H-imidazo[4,5-c]quinoline-2-methanol (3 g; 9.2 mmol, Example 60) and the resulting mixture was stirred for about 2 hours.

Methyl iodide (0.82 mL; 13.8 mmol) was added to the mixture and stirring was continued overnight. Thin layer chromatography indicated that the reaction was incomplete so sodium hydride (0.25 g) was added followed two hours later by methyl iodide (1 mL). The reaction was stirred for several additional hours then quenched with water and diluted with ethyl acetate. The organic layer was separated, washed with water, dried over magnesium sulfate and concentrated under vacuum to provide an oil. The oil was purified by silica gel chromatography (1–3% methanol in methylene chloride as eluent) to provide 0.5 g of a solid, m.p. 125°–128° C. Analysis: Calculated: C, 70.55; H, 8.3; % N, 16.5; Found: C, 70.2; H, 8.3; N, 16.0.

EXAMPLE 62

2-[1-(1-Morpholino)pentyl]-1°-2-methylpropyl)-1H-imidazo[4,5-c]quinolin-4-amine

Thionyl chloride (1 mL; 13.8 mmol) was added to a chilled (0°–5° C.) suspension of 4-amino-α-butyl-1-(2-methylpropyl)-1H-imidazo[4,5-c]quinoline-2-methanol (3 g; 9.2 mmol, Example 60) in methylene chloride (30 mL). The resulting mixture was stirred for several hours. Morpholine (8 mL; 90 mmol) was added and the reaction mixture was heated at reflux until thin layer chromatography indicated that the reaction was complete. The reaction mixture was diluted with additional methylene chloride, then water and ammonium hydroxide were added. The organic layer was separated, washed with water, dried over magnesium sulfate and concentrated under vacuum. The residue was purified by sequential silica gel chromatography using ethyl acetate as the eluent in the first column and 1–4% methanol in methylene chloride as the eluent in the second column to give about 1 g of the desired product as a solid m.p. 95°–100° C. which analyzes for a third of a mole of water. Analysis: Calculated: C, 68.8, H, 8.45; N, 17.4; Found: C, 68.7; H, 8.1; N, 17.4.

EXAMPLE 63

α-Methyl-1-(2-methylpropyl)-1H-imidazo[4,5-c]quinoline-2-methanol

Using the general method of Example 45, 1-(2-methylpropyl)-1H-imidazo[4,5-c]quinoline (20 g; 89 mmol) was reacted with acetaldehyde to provide the desired product. The structure was confirmed by nuclear magnetic resonance spectroscopy.

EXAMPLE 64

2-(1-Methoxyethyl)-1-(2-methylpropyl)-1H-imidazo[4,5-c]quinoline

Using the general method of Example 49, α-methyl-1-(2-methylpropyl)-1H-imidazo[4,5-c]quinoline-2-methanol (3 g; 11 mmol, Example 63) was reacted with methyl iodide to provide 2.4 g of the desired product. The structure was confirmed by nuclear magnetic resonance spectroscopy.

EXAMPLE 65

2-(1-Methoxyethyl)-1-(2-methylpropyl)-1H-imidazo[4,5-c]quinoline 5N Oxide

Using the general method of Example 50, 2-(1-Methoxyethyl)-1-(2-methylpropyl)-1H-imidazo[4,5-c]quinoline (2.4 g; 8.5 mmol, Example 64) was oxidized using peracetic acid to provide the desired 5N oxide.

EXAMPLE 66

2(1-Methoxyethyl)-1-(2-methylpropyl)-1H-imidazo[4,5-c]quinolin-4-amine

Using the general method of Example 51, 2-(1-methoxyethyl)-1-(2-methylpropyl)-1H-imidazo[4,5-c]quinoline 5N oxide (2.4 g; 8 mmol, Example 65) was aminated to provide 1 g of the desired product as a crystalline solid, m.p. 185°–189° C. which analyzes for one fourth of a mole of water. Analysis: Calculated: C, 67.4; H, 7.5; N, 18.5; Found: C, 67.7; H, 7.4; N, 18.1.

EXAMPLE 67

α-Methyl-1-(2-methylpropyl)-1H-imidazo[4,5-c]quinoline-2-methyl Acetate

Using the general method of Example 46, α-methyl-1-(2-methylpropyl)-1H-imidazo[4,5-c]-quinoline-2-methanol (5.8 g, 0.02 mol, Example 16) was reacted with acetic anhydride to provide the desired product.

EXAMPLE 68

2-(1-Acetoxyethyl)-1°-2-methylpropyl)-1H-imidazo[4,5-c]quinoline 5N Oxide

Using the general method of Example 47 α-methyl-1-(2-methylpropyl)-1H-imidazo[4,5-c]-quinoline-2-methyl acetate, (6.3 g 0.02 mol, Example 67) was oxidized with peracetic acid to provide the desired 5N oxide as a solid. The structure was confirmed by nuclear magnetic resonance spectroscopy.

EXAMPLE 69

4-Amino-α-methyl-1-(2-methylpropyl)-1H-imidazo[4,5,c]quinoline-2-methyl Acetate Hydrate Using the general method of Example 51, 2-(1-acetoxyethyl)-1-(2-methylpropyl)-1H-imidazo[4,5c]quinoline 5N oxide (4.1 g 2.5 mmol, Example 68) was aminated to provide the desired product as a solid, m.p. 152°–155° C. which analyzes as containing one fourth of a mole of water. Analysis: Calculated % C 65.3; % H, 6.8; % N, 16.9; Found: % C, 65.5; % H, 6.8; % N, 16.9.

EXAMPLE 70

2-(2-Methoxyethyl)-1-(2-methylpropyl)-1H-imidazo[4,5-c]quinoline

Using the general method of Example 45, 2-methyl-1-(2-methylpropyl)-1H-imidazo[4,5-c]quinoline (2 g 8.4 mmol,) was reacted with 2chloroethyl methyl ether (0.76 mL, 10 mmol) to provide the desired product. The structure was confirmed by nuclear magnetic resonance spectroscopy.

EXAMPLE 71

2-(2-Methoxyethyl)-1-(2-methylpropyl)-1H-imidazo[4,5-c]quinoline 5N Oxide

Using the general method of Example 47, 2-(2-methoxyethyl)-1-(2-methylpropyl)-1H-imidazo[4,5-c]quinoline (1 g, 3.5 mmol, Example 70) was oxidized with peracetic acid to provide 0.75 g of the desired 5N oxide as a yellow solid. The structure was confirmed by nuclear magnetic resonance spectroscopy.

EXAMPLE 72

2-(2-Methoxyethyl)-1-(2-methylpropyl)-1H-imidazo[4,5-c]quinolin-4-amine

Using the general method of Example 51, 2-(2-methoxyethyl)-1-(2-methylpropyl)-1H-imidazo[4,5c]quinoline 5N oxide (0.75 g, Example 71) was aminated to provide 0.4 g of the desired product as a solid, m.p. 168°–170° C. Analysis: Calculated: % C, 68.4; % H, 7.4; % N, 18.8; Found: % C, 68.4; % H, 7.4; % N, 18.6.

EXAMPLE 73

1-[1-(2-Methylpropyl)-1H-imidazo[4,5-c]quinolin-2-yl]propan-2-one

2-Methyl-1-(2-methylpropyl)-1H-imidazo[4,5c]quinoline (1 g, 4.2 mmol) was dissolved in anhydrous tetrahydrofuran (20 mL) then cooled to −78° C. A portion of lithium diisopropyl amide (2.8 mL, 4.2 mmol) was added dropwise to the cooled solution. At 10 minutes post addition, N-methoxy-N-methylacetamide (0.45 g, 4.4 mmol), prepared according to the method of T. A. Oster and T. M. Harris, *Tetrahedron Letters*, 24, 1851 (1983) was added. After 15 minutes the reaction was quenched with water and the resulting precipitate was collected and dried to provide the desired product as a solid. The structure was confirmed by nuclear magnetic resonance spectroscopy.

EXAMPLE 74

α-Methyl-1-(2-methylpropyl)-1H-imidazo[4,5-c]quinoline-2-ethanol

1-[1-(2-Methylpropyl)-1H-imidazo[4,5c]quinolin-2-yl] propan-2-one (8 g, 28.4 mmol, Example 73) was suspended in ethanol (400 mL). Sodium borohydride (1.64 g, 43.3 mmol) was added and the reaction mixture was stirred at room temperature for about 2 hours. Methanol (about 20 mL) was added and stirring was continued over night. Water was added then the solvents were removed under vacuum. The residue was partitioned between methylene chloride and water. The methylene chloride layer was separated, dried over magnesium sulfate then concentrated under vacuum to give the desired product. The structure was confirmed by nuclear magnetic resonance spectroscopy.

EXAMPLE 75

2-(2-Methoxypropyl)-1-(2-methylpropyl)-1H-imidazo[4,5-c]guinoline

α-Methyl-1-(2-methylpropyl)-1H-imidazo[4,5-c]quinoline-2-ethanol (6.5 g, 23 mmol, Example 74) was dissolved in N,N-dimethylformamide (50 mL) then cooled to 0° C. Sodium hydride (0.8 g, 25 mmol), 80% dispersion in mineral oil) was added and the resulting mixture was stirred at 0° C. for about 1 hour. Methyl iodide (2.2 mL, 34 mmol) was added and the resulting mixture was stirred at 0° C. for about 1 hour and then allowed to warm to room temperature. The reaction was quenched with water and then diluted with ethyl acetate. The organic layer was separated, washed several times with water, dried over magnesium sulfate then concentrated under vacuum. The resulting residue was purified by silica gel chromatography using 2–5% methanol in methylene chloride to give about 3 g of the desired product. The structure was confirmed by nuclear magnetic resonance spectroscopy.

EXAMPLE 76

2-(2-Methoxypropyl)-1-(2-methylpropyl)-1H-imidazo[4,5-c]quinoline 5N Oxide

Using the general method of Example 47, 2-(2-methoxypropyl)-1-(2-methylpropyl)-1H-imidazo[4,5c]quinoline (3 g, 10 mmol, Example 75) was oxidized with peracetic acid to provide 2.1 g of the desired 5N oxide as a solid, m.p. 125°–130° C. The structure was confirmed by nuclear magnetic resonance spectroscopy.

EXAMPLE 77

2-(2-Methoxypropyl)-1-(2-methylpropyl)-1H-imidazo[4,5-c]quinolin-4-amine

Using the general method of Example 51, 2-(2-methoxypropyl)-1-(2-methylpropyl)-1H-imidazo[4,5-c]quinoline 5N oxide (2 g, 6.4 mmol, Example 76) was aminated to provide 1.3 g of the desired product as a solid, m.p. 139°–141° C. Analysis: Calculated: % C, 69.2; % H, 7.7; % N, 17.9; Found: % C, 69.1; % H, 7.8; % N, 17.8.

EXAMPLE 78

α-Methyl-1-(2-methylpropyl)-1H-imidazo[4,5-c]quinoline-2-ethyl Acetate

Using the general method of Example 46, α-methyl-1-(2-methylpropyl)-1H-imidazo[4,5-c]quinoline-2-ethanol (9.4 g, 33 mmol, Example 74) was reacted with acetic anhydride to provide the desired product. The structure was confirmed by nuclear magnetic resonance spectroscopy.

EXAMPLE 79

2-(2-Acetoxypropyl)-1-(2-methylpropyl)-1H-imidazo[4,5-c]quinoline 5N Oxide

Using the general method of Example 47, α-methyl-1-(2-methylpropyl)-1H-imidazo[4,5-c]quinoline-2-ethyl acetate (10.7 g, 33 mmol, Example 78) was oxidized with peracetic acid to provide the desired 5N oxide. The structure was confirmed by nuclear magnetic resonance spectroscopy.

EXAMPLE 80

4-Amino-a-methyl-1-(2-methylpropyl)-1H-imidazo[4,5-c]quinoline-2-ethyl Acetate Using the general method of Example 51, 2-(2-acetoxypropyl)-1-(2-methylpropyl)-1H-imidazo[4,5-c]quinoline 5N oxide (10.5 g, 30 mmol, Example 79) was aminated to provide the desired product. The structure was confirmed by nuclear magnetic resonance spectroscopy.

EXAMPLE 81

4-Amino-α-methyl-1-(2-methylpropyl)-1H-imidazo[4,5-c]quinoline-2-ethanol

Using the general method of Example 60, 4-amino-α-methyl-1-(2-methylpropyl)-1H-imidazo[4,5-c]quinoline-2-ethyl acetate (10.2 g, 30 mmol, Example 80) was hydrolyzed to provide 2 g of the desired product as a solid, m.p. 196°–197.5° C. Analysis: Calculated: % C, 68.4; % H, 7.4; % N, 18.8; Found: % C, 68.6; % H, 7.5; % N, 18.9.

EXAMPLE 82

7-Chloro-4-(2-hydroxy-2-methylpropylamino)-3-nitroquinoline

Using the general method of Example 41, 7-chloro-4-hydroxy-3-nitroquinoline (18 g, 80 mmol,) was chlorinated using thionyl chloride. After the chlorination was complete, as indicated by thin layer chromatography, the reaction mixture was allowed to cool to room temperature. Triethylamine (28 mL, 200 mmol) and 2-amino-2-methyl-2-propanol (10.3 g, 96 mmol) were added and the reaction mixture was heated at reflux for about 1 hour. The reaction mixture was cooled in an ice bath and the resulting precipitate was collected and dried to provide the desired product as a solid. The structure was confirmed by nuclear magnetic resonance spectroscopy.

EXAMPLE 83

7-Chloro-α,α-dimethyl-2-ethoxymethyl-1H-imidazo[4,5-c]quinoline-1-ethanol

Using the general method of Example 42, 7-chloro-4-(2-hydroxy-2-methylpropylamino)-3nitroquinoline (18.5 g, 63 mmol, Example 82) was reduced and the resulting diamine reacted with ethoxyacetic acid to provide the desired product as a thick, green oil.

EXAMPLE 84

7-Chloro-2-ethoxymethyl-1-(2-hydroxy-2-methylpropyl)-1H-imidazo[4,5-c]quinoline 5N Oxide Using the general method of Example 47, 7-chloro-α,α-dimethyl-2-ethoxymethyl-1H-imidazo[4,5-c]quinoline-1-ethanol (20.9 g, 63 mmol, Example 83 ) was oxidized with peracetic acid to provide 14.8 g of the desired oxide as a solid.

EXAMPLE 85

4-Amino-7-chloro-α,α-dimethyl-2-ethoxymethyl-1H-imidazo[4,5-c]quinoline-1-ethanol Using the general method of Example 51, 7-chloro-2-ethoxymethyl-1-(2-hydroxy-2-methylpropyl)-1H-imidazo[4,5-c]quinoline 5N oxide (14.8 g, 42 mmol, Example 84) was aminated to provide 8.6 g of the desired product as a solid, m.p. 238°–240° C. Analysis: Calculated: % C, 58.5; % H, 6.1; % N, 16.1; Found: % C, 58.4; % H, 6.0; % N 16.0.

EXAMPLE 86

α,α-Dimethyl-2-hydroxymethyl-1H-imidazo[4,5-c]quinoline-1-ethanol

Using the general method of Example 24, 3-amino-4-(2-hydroxy-2-methylpropylamino)quinoline (45 g, 0.19 mol) was reacted with glycolic acid to provide 35.7 g of the desired product as a tan solid. The structure was confirmed by nuclear magnetic resonance spectroscopy.

EXAMPLE 87

1-(2-Hydroxy-2-methylpropyl)-1H-imidazo[4,5-c]quinoline-2-methyl Acetate

Using the general method of Example 2, α,α-dimethyl-2-hydroxymethyl-1H-imidazo[4,5-c]quinoline-1-ethanol (35.0 g, 0.13 mol, Example 86) was reacted with acetyl chloride to provide 32.3 g of a tan solid. Nuclear magnetic resonance spectroscopy showed that the tan solid contained the desired product plus about 10 percent of the diester. The material was used without additional purification.

EXAMPLE 88

2-Acetoxymethyl-1-(2-hydroxy-2-methylpropyl)-1H-imidazo[4,5-c]quinoline 5N Oxide Using the general method of Example 47, 1-(2-hydroxy-2-methylpropyl)-1H-imidazo[4,5-c]quinoline-2-methyl acetate (31 g, Example 87) was oxidized with peracetic acid to provide 19.6 g of crude 5N oxide.

EXAMPLE 89

4-Chloro-1-(2-hydroxy-2-methylpropyl)-1H-imidazo[4,5-c]quinoline-2-methyl Acetate A 16.7 g portion of the crude 5N oxide prepared in Example 88 was suspended in methylene chloride (1200 mL). Phosphorous oxychloride (3.5 mL) was added to the suspension with vigorous stirring over a period of about 5 minutes. After about 1.5 hours, the reaction mixture was filtered to remove 7.9 g of a solid. The methylene chloride liltrate was combined with phosphorous oxychloride (1.2 mL) and stirred at room temperature for about 20 hours. Saturated sodium bicarbonate solution (250 mL) was added with stirring to the reaction mixture. The layers were separated. The aqueous layer was extracted with methylene chloride. The methylene chloride layers were combined, dried over magnesium sulfate and concentrated under vacuum to provide 10.2 g the desired product as a tan solid. The structure was confirmed by nuclear magnetic resonance spectroscopy.

EXAMPLE 90

4-Amino-α,α-dimethyl-2-hydroxymethyl-1H-imidazo[4,5-c]quinoline-1-ethanol

Using the general method of Example 9, 4-chloro-1-(2-hydroxy-2-methylpropyl)-1H-imidazo[4,5-c]quinoline-2-methyl acetate (8.3 g, 24 mmol, Example 89) was aminated to provide 2.3 g of the desired product as a solid, m.p. 264°–271° C. Analysis: Calculated: % C, 62.9; % H, 6.3; % N, 19.6; Found: % C, 62.9; % H, 6.3; % N, 19.3.

EXAMPLE 91

2-Ethoxymethyl-1-phenylmethyl-1H-imidazo[4,5-c]quinoline

3-Amino-4-(phenylmethylamino)quinoline (4 g, mmol) was combined with ethoxyacetic acid (4.5 mL, mmol) and heated at 120° C. for about 3 hours. The reaction mixture was cooled to room temperature, diluted with water and then made basic with ammonium hydroxide. The resulting precipitate was collected to provide 5.3 g of the desired product as a solid. The structure was confirmed by nuclear magnetic resonance spectroscopy.

EXAMPLE 92

2-Ethoxymethyl-1-phenylmethyl-
1H-imidazo[4,5-c]quinoline 5N Oxide

Using the general method of Example 47, 2-ethoxymethyl-1-phenylmethyl-1H-imidazo[4,5-c]quinoline (4.5 g, 14 mmol, Example 91) was oxidized with peracetic acid to provide 3.2 g of the desired 5N oxide as a solid.

EXAMPLE 93

2-Ethoxymethyl-1-phenylmethyl-1H-imidazo[4,5-c] quinolin-4-amine

Using the general method of Example 51, 2-ethoxymethyl-1-phenylmethyl-1H-imidazo[4,5-c]quinoline 5N oxide (3.2 g, 9.6 mmol, Example 92) was aminated to provide 1.1 g of the desired product as a solid, m.p. 204°–205° C. Analysis: Calculated: % C, 72.3; % H, 6.1; % N, 16.9; Found: % C, 72.1; % H, 5.7; % N, 16.6.

EXAMPLE 94

α,α-Dimethyl-2-methoxymethyl-
1H-imidazo[4,5-c]quinoline-1-ethanol

3-Amino-4-(2-hydroxy-2methylpropylamino)quinoline (7.5 g, 32 mmol) was combined with methoxyacetic acid (7.5 mL, 97 mmol) and heated at about 170° C. for about 3 hours. The resulting solid residue was dissolved in ethyl acetate (150 mL). The ethyl acetate solution was extracted twice with 0.2N sodium hydroxide, washed with water, dried over magnesium sulfate, treated with activated charcoal and then concentrated to a volume of about 50 mL. Hexane was added to the ethyl acetate and the resulting precipitate was collected and dried to provide 0.9 g of the desired product as a crystalline solid, m.p. 145°–148° C. Analysis: Calculated: % C, 67.3; % H, 6.7; % N, 14.7; Found: % C, 67.2; % H, 6.6; % N, 14.6.

EXAMPLE 95

1-(2-Hydroxy-2-methylpropyl)-2-methoxymethyl-
1H-imidazo[4,5-c]quinoline 5N Oxide Using the general method of Example 47, α,α-dimethyl-2-methoxymethyl-1H-imidazo[4,5-c]quinoline-1-ethanol (6.6 g, 23 mmol, Example 94) was oxidized with peracetic acid to provide 5.7 g of the desired 5N oxide. A small sample was recrystallized from ethyl acetate to provide an analytical sample, m.p. 175°–197° C. Analysis: Calculated: % C, 63.8; % H, 6.4; % N, 14.0; Found: % C, 63.8; % H, 6.4; % N, 13.8.

EXAMPLE 96

4-Amino-α,α-dimethyl-2-methoxymethyl-1H-imidazo
[4,5-c ]quinoline-1-ethanol

Using the general method of Example 51, 1-(2-hydroxy-2-methylpropyl) -2-methoxymethyl-1H-imidazo[4,5c] quinoline 5N oxide (4.7 g, 16 mmol, Example 95) was aminated to provide 2.4 g of the desired product as a solid, m.p. 204°–207° C. Analysis: Calculated: % C, 64.0; % H, 6.7; % N, 18.6; Found: % C, 64.1; % H, 6.8; % N, 18.6.

EXAMPLE 97

α,α-Dimethyl-2-ethoxymethyl-
1H-imidazo[4,5-c]quinoline-1-ethanol

Using the general method of Example 91, 3-amino-4-(2-hydroxy-2-methylpropylamino)quinoline (46.2 g. 0.20 mol) was reacted with ethoxyacetic acid (62.5 g, 0.6 mol) to provide 53.6 g of crude product as a greyish solid. A small amount was recrystallized from toluene to provide 3.6 g of a colorless solid, m.p. 117°–120° C. Analysis: Calculated: % C 68.2; % H, 7.1; % N, 14.0; Found: % C, 68.5; % H, 7.1; % N, 14.0.

EXAMPLE 98

2-Ethoxymethyl-1-(2-Hydroxy-2-methylpropyl)-1H-imidazo[4,5-c]quinoline 5N Oxide

Using the general method of Example 47, α,α-dimethyl-2-ethoxymethyl-1H-imidazo[4,5-c]quinoline-1-ethanol (59.9 g, 0.2 mol, Example 97) was oxidized with peracetic acid to provide 59.9 g of crude 5N oxide as a solid.

EXAMPLE 99

4-Amino-α,α-dimethyl-2-ethoxymethyl-
1H-imidazo[4,5-c]quinoline-1-ethanol

Using the general method of Example 51, 2-ethoxymethyl-1- ( 2-hydroxy-2-methylpropyl ) -1Himidazo[4,5-c] quinoline 5N oxide (30.0 g, 0.095 mol, Example 98) was aminated to provide 25.7 g of crude product as an off white solid. A portion (20.3 g) of the crude product was suspended in methanol (125 mL) and methylene chloride (60 mL) was added to the suspension. The resulting solution was treated with charcoal then filtered. The filtrate was evaporated under heat to remove the methylene chloride and reduce the total volume to about 110 mL. The solution was then allowed to cool to room temperature. The resulting precipitate was collected, rinsed with methanol and dried to provide 12.1 g of the desired product as a colorless crystalline solid, m.p. 190°–193° C. Analysis: Calculated: % C, 65.0; % H, 7.1; % N, 17.8; Found: % C, 64.8; % H, 7.1; % N, 17.9.

EXAMPLE 100

4-Chloro-α,α-dimethyl-2-ethoxymethyl-
1H-imidazo[4,5-c]quinoline-1-ethanol

3-Amino-2-chloro-4-(2-hydroxy-2-methylpropylamino-)quinoline (2.0 g, 7.5 mmol) was combined with acetonitrile (80 mL). Ethoxyacetyl chloride (0.92 g, 7.5 mmol) was added to the reaction mixture. After about 5 minutes a yellow precipitate formed. p-Toluenesulfonic acid (0.1 g) was added and the reaction mixture was heated to reflux. Refluxing was continued for about 120 hours at which time the reaction mixture was homogeneous. The reaction mixture was cooled and the acetonitrile was removed under vacuum. The resulting residue was dissolved in methylene chloride and washed with dilute ammonium hydroxide. The aqueous phase was extracted with methylene chloride (3×25 mL). The organic phases were combined, dried over magnesium sulfate and then concentrated to provide 2.6 g of crude product as a dark yellow solid. The crude product was recrystallized from t-butylmethyl ether to provide 1.8 g of a solid. The structure was confirmed by nuclear magnetic resonance spectroscopy.

EXAMPLE 101

4-Amino-e,e-dimethyl-2-ethoxymethyl-1H-imidazo[4,5-c]quinoline-1-ethanol

4-Chloro-α,α-dimethyl-2-ethoxymethyl-1H-imidazo[4,5-c]quinoline-1-ethanol (1.0 g, 3 mmol, Example 100) and 7% methanolic ammonia (30 mL) were placed in a steel pressure vessel at about 150°–160° C. for 6 hours. The vessel was cooled to below room temperature and the reaction solution removed and treated with methanolic potassium hydroxide. The solution was then evaporated to a low volume and diluted with water. The resulting precipitate was collected, washed with water and dried to provide 0.7 g of the crude product as a solid. The crude product was recrystallized from a mixture of ethyl acetate and methanol to provide a colorless solid.

EXAMPLE 102

2-Methoxymethyl-1-phenylmethyl-1H-imidazo.[4,5-c]quinoline

Using the general method of Example 91, 3-amino-4-(phenylmethylamino)quinoline (4.0 g, 16 mmol) was reacted with methoxyacetic acid (3.7 mL) to provide 4.4 g of the desired product as a solid. The structure was confirmed by nuclear magnetic resonance spectroscopy.

EXAMPLE 103

2-Methoxymethyl-1-phenylmethyl-1H-imidazo[4,5-c]quinoline 5N Oxide

Using the general method of Example 47, 2-methoxymethyl-1-phenylmethyl-1H-imidazo[4,5-c]quinoline (4.4 g, 14.5 mmol, Example 102) was oxidized with peracetic acid to provide 3 g of the desired 5N oxide as a solid.

EXAMPLE 104

2-Methoxyethyl-1-phenylmethyl-1H-imidazo[4,5-c]quinolin-4-amine

Using the general method of Example 51, 2-methoxymethyl-1-phenylmethyl-1H-imidazo[4,5-c]quinoline 5N oxide (3 g, 9 mmol, Example 103) was aminated to provide 2.0 g of the desired product as a solid, m.p. 202°–204° C. Analysis: Calculated: % C, 71.7; % H, 5.7; % N, 17.6; Found: % C, 71.4; % H, 5.7; % N, 17.4.

EXAMPLE 105

4.-(3-Methylbutylamino)-3-nitroquinoline

Using the general method of Example 41, 4-hydroxy-3-nitroquinoline (19 g, 0.10 mole) was chlorinated and then reacted with isoamylamine (10.5 g, 0.12 mole) to provide the crude product as a yellow solid. This solid was recrystallized from hexane to provide the desired product as a solid, m.p. 99°–100° C. Analysis: Calculated: % C, 64.8; % H, 6.6; % N, 16.2; Found: % C, 64.8; % H, 6.6; % N, 16.1.

EXAMPLE 106

3-Amino-4-(3-methylbutylamino)quinoline 4-(3-Methylbutylamino)-3-nitroquinoline (10 g, 0.04 mole; Example 105) was combined with toluene (300 mL), 5% palladium on carbon (1 g) and magnesium sulfate. The mixture was hydrogenated on a Parr apparatus at an initial pressure of 47 psi (3.3 Kg/cm$^2$). When the hydrogenation was complete, the solids were removed by filtration and the filtrate was evaporated to provide the diamine. A sample (1.5 g) was recrystallized from hexane to provide the desired product as a solid, m.p. 92°–94° C. Analysis: Calculated: % C, 73.3; % H, 8.4; % N, 18.3; Found: % C, 73.0; % H, 8.3; % N, 18.3.

EXAMPLE 107

2-Ethoxymethyl-1-(3-methylbutyl)-1H-imidazo[4,5-c]quinoline

3-Amino-4-(3-methylbutylamino)quinoline (7 g, 0.03 mole; Example 106) was combined with ethoxyacetic acid (8 mL, 0.08 mole) and heated at 150°–160° C. for about 2 hours. The reaction mixture was cooled to room temperature, diluted with water (100 mL), made basic with sodium hydroxide and then extracted with ethyl acetate. The extract was dried over magnesium sulfate then evaporated to provide the crude product as a crystalline solid. The solid was recrystallized from hexane to provide the desired product as a solid, m.p. 64°–65° C. Analysis: Calculated: % C, 72.7; % H, 7.8; % N, 14.1; Found: % C, 72.5; % H, 7.7; % N, 14.1.

EXAMPLE 108

2-Ethoxymethyl-1-(3-methylbutyl)-1H-imidaz[4,5-c]quinoline 5N Oxide

2-Ethoxymethyl-1-(3-methylbutyl)-1H-imidazo[4,5-c]quinoline (6 g, 0.02 mole, Example 107) was dissolved in methyl acetate (60 mL) then combined with peracetic acid (8.4 g, 0.04 mole) and heated until the reaction was complete as determined by thin layer chromatography (silica gel, ethyl acetate). The reaction mixture was evaporated. The residue was azeotroped 5 times with heptane (250 mL) to provide the desired 5N oxide.

EXAMPLE 109

2-Ethoxymethyl-1-(3-methylbutyl)-1H-imidazo[4,5-c]quinolin-4-amine Hydrochloride Using the general method of Example 51, 2-ethoxymethyl-1-(3-methylbutyl)-1H-imidazo[4,5c]quinoline 5N oxide (6 g, 0.02 mole, Example 108) was aminated to provide the desired product as a solid, m.p. 291°–292° C. Analysis: Calculated: % C, 62.0; % H, 7.2; % N, 16.0; Found: % C, 62.0; % H, 7.1; % N, 16.0.

EXAMPLE 110

N-[2-Chloro-4-(2-hydroxy-2-methylpropyl)amino-3-quinolinyl]-3-methoxypropanamide 3-Methoxypropionyl chloride (5.5 g, 0.045 mole) was slowly added with stirring to a solution of 1[(3-amino-2-chloro-4-quinolinyl)amino]-2-methyl-2propanol (10 g, 0.038 mole) in acetonitrile (140 mL). After the addition was completed, the reaction mixture was heated at reflux for 30 minutes then allowed to stir at room temperature overnight. The reaction mixture was filtered to provide 12.4 g of the desired product as a solid.

EXAMPLE 111

4-Amino-α,α-dimethyl-2-methoxymethyl-1H-imidazo[4x5-c]quinoline-1-ethanol

N-[2-Chloro-4-(2-hydroxy-2-methylpropyl)amino-3-quinolinyl]-3-methoxypropanamide (6 g, Example 110) was added to 5% ammonia in methanol (60 mL). The mixture was heated in a Parr bomb for 5 hours at approximately 150° C. The solvent was evaporated under vacuum to give a brown residue. The residue was diluted with water and sodium bicarbonate then extracted with ethyl acetate. The ethyl acetate extract was washed with water, dried over magnesium sulfate then evaporated to provide a tan solid. The solid was purified by silica gel chromatography to provide 1.64 g of the desired product as a solid, m.p. 174°–175° C. Analysis: Calculated: % C, 65.0; % H, 7.0; % N, 17.8; Found: % C, 64.8; % H, 7.0; % N, 17.7.

EXAMPLE 112

3-Butylamino-2-chloro-3-nitroquinoline

Triethylamine (37.8 g, 0.37 mole) was added with stirring to a suspension of 4-hydroxy-3-nitro-2(1H)-quinolinone (50 g, 0.24 mole) in toluene (175 mL) while maintaining the temperature of the reaction mixture below 40° C. After the addition was complete, the reaction mixture was cooled to 15° C. and phosphorous oxychloride (152 g, 0.99 mole) was added while maintaining the temperature of the reaction mixture below 55° C. After the addition was complete, the reaction mixture was refluxed at 110° C. until the reaction was complete as determined by thin layer chromatography (silica gel; 50:50 ethyl acetate:hexanes). The reaction mixture was allowed to cool to room temperature and was then poured into a mixture of ice and water (400 mL). The mixture was stirred for 1 hour. The phases were separated and the aqueous phase was extracted twice with toluene. The toluene extracts were combined with the organic phase, washed with water, filtered to remove a small amount of solid then dried over magnesium sulfate to give a solution of the dichloro intermediate in toluene. This solution was combined with triethylamine (25.5 g, 0.25 mole) then stirred for 15 minutes. n-Butylamine (21.3 g, 0.29 mole) was added and the reaction mixture was heated at 50° C. for 90 minutes. The reaction mixture was allowed to cool to room temperature, combined with concentrated hydrochloric acid (71 mL) then stirred at room temperature for 1 hour. The resulting solid was collected by filtration, rinsed with acetone then slurried with acetone to provide the hydrochloride salt of the desired product as a yellow solid. The solid was added to a cooled solution of sodium hydroxide (40 g) in water (200 mL) and stirred for 1 hour. The solid was collected by filtration, rinsed with water and dried at 45° C. under vacuum to provide 34 g of the desired product. A 1 g portion was recrystallized from toluene to provide a sample for analysis. Analysis: Calculated: % C, 55.8; % H, 5.0; % N, 15.0; Found: % C, 55.6; % H, 5.0; % N, 14.9.

EXAMPLE 113

3-Amino-4-butylamino-2-chloroquinoline

4-Butylamino-2-chloro-3-nitroquinoline (33 g, 0.12 mole, Example 112) was combined with toluene (200 mL) and 5% platinum on carbon (1 g). The mixture was hydrogenated on a Parr apparatus at an initial pressure of 38 psi (2.7 Kg/cm2). When the hydrogenation was complete, the catalyst was removed by filtration and the filtrate was concentrated to provide a brown liquid. The liquid was chilled in an ice bath to provide an orange solid. The solid was collected by filtration, slurried with diethyl ether for 30 minutes then filtered to provide 20 g of the desired product as a tan solid. The structure was confirmed by nuclear magnetic resonance spectroscopy.

EXAMPLE 114

N-(4-Butylamino-2-chloro-3-quinolinyl)-3-methoxypropanamide

Using the general method of Example 110, 3-amino-4-butylamino-2-chloroquinoline (10 g, 0.04 mole, Example 113) was reacted with 3-methoxypropionyl chloride to provide 10.3 g of the desired product as a yellow solid.

EXAMPLE 115

1-Butyl-2-methoxyethyl-1H-imidazo[4,5-c]quinolin-4-amine

Using the general method of Example 111, N-(4-butylamino-2-chloro-3-quinolinyl)-3-methoxypropanamide (10 g, 0.027 mole, Example 114) was cyclized and aminated to provide the desired product as a solid, m.p. 149°–151° C. Analysis: Calculated: % C, 68.4; % H, 7.4; % N, 18.8; Found: % C, 68.5; % H, 7.3; % N, 18.7.

EXAMPLE 116

N-(4-Butylamino-2-chloro-3-quinolinyl)ethoxyacetamide

Using the general method of Example 110, 3-amino-4-butylamino-2-chloroquinoline (10 g, 0.04 mole, Example 113) was reacted with ethoxyacetyl chloride to provide 9.8 g of the desired product as a yellow solid.

EXAMPLE 117

1-Butyl-2-ethoxymethyl-1H-imidazo[4,5-c]quinolin-4-amine

Using the general method of Example 111, N-(4-butylamino-2-chloro-3-quinolinyl)ethoxyacetamide (9 g, 0.024 mole, Example 116) was cyclized and aminated to provide 1.9 g of the desired product as a solid, m.p. 139°–140° C. Analysis: Calculated: % C, 68.4; % H, 7.4; % N, 18.8; Found: % C, 68.6; % H, 7.3; % N, 18.9.

EXAMPLE 118

4-[(2-Chloro-3-nitro-4-quinolinyl)amino]-3-methyl-1-butene-3-ol

Triethyl amine (6.2 mL, 0.045 mole) was added to a solution of 2,4-dichloro-3-nitroquinoline (10.9 g, 0.045 mole) in methylene chloride (60 mL). 4-Amino-3-methyl-1-butene-3-ol was added and the reaction mixture was heated at reflux for several hours before being concentrated under vacuum. The residue was chilled in an ice bath to give a solid. The solid was recrystallized from toluene to provide 17.1 g of the desired product as a yellow solid. The structure was confirmed by nuclear magnetic resonance spectroscopy.

EXAMPLE 119

1-[l3-Amino-2-chloro-4-quinolinyl)amino]-α-ethyl-α-methylethanol

4-[(2-Chloro-3-nitro-4-quinolinyl)amino]-3-methyl-1-butene-3-ol (10.8 g, 0.035 mole, Example 118) was combined with ethanol (300 mL) and 0.5 g 5% platinum on carbon. The mixture was hydrogenated on a Parr apparatus. The reaction mixture was filtered through celite and the filtrate was concentrated to provide an oil. The oil was purified by silica gel column chromatography. An attempt to crystallize the purified oil using ethanol and water produced an oil. The mixture was concentrated under vacuum with toluene then extracted with methylene chloride. The methylene chloride extract was dried over magnesium sulfate then concentrated under vacuum to provide 6.6 g of the desired product as a solid, m.p. 99°–101° C. Analysis: Calculated: % C, 60.1; % H, 6.5; % N, 15.0; Found: % C, 60.0; % H, 6.4; % N, 14.8.

EXAMPLE 120

N-[2-Chloro-4-(2-hydroxy-2-methylbutyl)amino-3-quinolinyl]ethoxyacetamide

Ethoxyacetyl chloride (0.93 g, 7.6 mmole) was added to a solution of 1-[(3-amino-2-chloro-4quinolinyl)amino]-α-ethyl-α-methylethanol (2 g, 7.2 mmole, Example 119) in methylene chloride (10 mL). The reaction mixture was heated at reflux for 30 minutes, cooled to room temperature, diluted with methylene chloride, extracted 3 times with aqueous sodium bicarbonate, dried over magnesium sulfate and then concentrated under vacuum to provide a liquid which solidified on standing. The solid was slurried with a mixture of toluene and hexane then isolated by filtration to provide 2.2 g of the desired product as a solid. The structure was confirmed by nuclear magnetic resonance spectroscopy.

EXAMPLE 121

4-Amino-2-ethoxymethyl-α-ethyl-α-methyl-1H-imidazo[4,5-c]quinoline-1-ethanol

Using the general method of Example 111, N-[2-chloro-4-(2-hydroxy-2-methylbutyl)amino-3-quinolinyl]ethoxyacetamide (2.1 g, 5.7 mmole, Example 120) was cyclized and aminated to provide 0.7 g of the desired product as a solid, m.p. 189°–191° C. Analysis: Calculated: % C, 65.8; % H 7.4; % N 17.1; Found: % C, 65.1; % H, 7.2; % N, 16.8.

EXAMPLE 122

N-Butyl-3-nitro-4-quinolinamine

Using the general method of Example 41, 4-hydroxy-3-nitroquinoline (38.4 g, 0.2 moles) was chlorinated then reacted with n-butylamine (24.7 mL, 0.4 mole) to provide the desired product as a yellow sold.

EXAMPLE 123

1-Butyl-1H-imidazo[4,5-c]quinoline-2-methanol

Using the general method of Example 1, N-butyl-3-nitro-4-quinolinamine (9.8 g, 0.04 mole, Example 122) was hydrogenated then reacted with glycolic acid (9.1 g, 0.12 mole) to provide 8.0 g of the desired product as a solid. A small sample was recrystallized from ethyl acetate to provide pure material, m.p. 146°–149° C. Analysis: Calculated: % C, 70.6; % H, 6.7; % N, 16.5; Found: % C, 70.3; % H, 6.7; % N, 16.3.

EXAMPLE 124

1-Butyl-1H-imidazo[4,5-c]quinoline-2-methyl Acetate

Using the general method of Example 46, 1-butyl-1H-imidazo[4,5-]quinoline-2-methanol (7.5 g, 0.029 mole, Example 123) was reacted with acetic anhydride to provide 8.2 g of the desired product as a solid. A small sample was recrystallized from ethyl acetate to provide a pure sample, m.p. 154°–157° C. Analysis: Calculated: % C, 68.7; % H, 6.4; % N, 14.1; Found: % C, 68.8; % H, 6.4; % N, 14.2.

EXAMPLE 125

1-Butyl-1H-imidazo[4,5-c]quinoline-2-methyl Acetate 5N Oxide Monohydrate

Using the general method of Example 108, 1-butyl-1H-imidazo[4,5-c]quinoline-2-methyl acetate (7.8 g, 0.026 mole, Example 124) was oxidized to provide 6.2 g of the crude 5N oxide as solid. A small sample was recrystallized from isopropanol to provide pure material, m.p. 184°–187° C. Analysis: Calculated: % C, 61.6; % H, 6.4; % N, 12.7; Found: % C, 61.8; % H, 6.2; % N, 12.6.

EXAMPLE 126

1-Butyl-4-chloro-1H-imidazo[4,5-c]quinoline-2-methyl Acetate

Using the general method of Example 6, 1-butyl-1H-imidazo[4,5-c]quinoline-2-methyl acetate 5N oxide monohydrate (6.0 g, 0.019 mole, Example 125) was chlorinated to provide a solid. The solid was purified by column chromatography (silica gel; ethyl acetate) to provide 3.7 g of the desired product as a solid. A 0.5 g portion was recrystallized from toluene to provide pure material, m.p. 169°–171° C. Analysis: Calculated: % C, 61.5; % H, 5.5; % N, 12.+; Found: % C, 61.4; % H, 5.4; % N, 12.5.

EXAMPLE 127

1-Butyl-4-chloro-1H-imidazo[4,5-c]quinoline-2-methanol

1-Butyl-4-chloro-1H-imidazo[4,5-c]quinoline-2-methyl acetate (3.1 g, 9.3 mmole, Example 126) was stirred overnight in 30 mL of 12% ammonia in methanol. The reaction mixture was concentrated under vacuum and the residue was slurried with water for about 30 minutes. The solid was collected by filtration and dried with toluene using a Dean-Stark trap to provide 2.2 g of the desired product, m.p. 184°–185° C. Analysis: Calculated: % C, 62.2; % H, 5.6; % N, 14.5; Found: % C, 62.0; % H, 5.5; % N, 14.3.

EXAMPLE 128

4-Amino-1-butyl-1H-imidazo[4,5-c]quinoline-2-methanol

1-Butyl-4-chloro-1H-imidazo[4,5-c]quinoline-2-methanol (2 g, 6.9 mmole, Example 127) was combined with 12 mL of 12% ammonia in methanol and heated in a Parr bomb at 160° C. for about 20 hours. The resulting solid was collected, rinsed with methanol then purified by silica gel chromatography using ethyl acetate/methanol as the eluent. The resulting solid was slurried with ethyl acetate, collected by filtration and dried to provide the desired product, m.p. 223°–225° C.

ANTIVIRAL ACTIVITY AND INTERFERON INDUCTION IN GUINEA PIGS

The test methods described below demonstrate the ability of compounds of the invention to reduce the number and severity of lesions developed by guinea pigs infected with Type II Herpes simplex virus and to induce the biosynthesis of interferon in guinea pigs.

Female Hartley guinea pigs weighing 200 to 250 g are anesthetized with methoxyflurane (available under the tradename METAFANE™ from Pitman-Moore, Inc., Washington Crossing, N.J.), after which the vaginal area is swabbed with a dry cotton swab. The guinea pigs are then infected intravaginally with a cotton swab saturated with Herpes simplex virus Type II strain 333 ($1 \times 10^5$ plaque forming units/mL). Guinea pigs are assigned to groups of 7 animals; one group for each treatment and one to serve as a control (vehicle treated). The compounds of the invention are formulated in water containing 5% Tween 80 (a polyoxyethylene sorbitan monooleate available from Aldrich Chemical Company, Inc., Milwaukee, Wis.). The guinea pigs are treated orally once daily for four consecutive days starting 24 hours after infection.

Antiviral Activity

Antiviral activity is evaluated by comparing lesion development in compound-treated versus vehicle-treated guinea pigs. External lesions are scored 4, 7, 8 and 9 days after infection using the following scale: 0—no lesion, 1—redness and swelling, 2—a few small vesicles, 3—several large vesicles, 4—large ulcers with necrosis and 5—paralysis. The maximum lesion score of each guinea pig is used to calculate the percentage lesion inhibition. The percentage lesion inhibition is calculated as follows:

$$100 - \left( \frac{\Sigma \text{ maximum lesion scores of treatment group} \times 100}{\Sigma \text{ maximum lesion scores of control group}} \right)$$

Interferon Induction

Twenty-four hours after the initial dose of test compound has been administered, blood is obtained from 3 guinea pigs from each treatment group by cardiac puncture of methoxyflurane anesthetized animals. Blood is pooled and allowed to clot at room temperature. After low speed centrifugation, serum is collected and stored at −70° C. until analysis.

Interferon levels in the guinea pig serum are determined in a standard microtiter assay using transformed guinea pig cells (ATCC CRL 1405). The interferon assay is done in 96 well microtiter plates. Confluent monolayers of transformed guinea pig cells are treated with dilutions of guinea pig serum made with medium 199 (GIBCO, Grand Island, N.Y.). The cell and serum dilutions are incubated at 37° C. overnight. The following day, the medium and serum are removed and about 10 plaque forming units of Mengovirus are added to each well. Controls consist of wells that receive no guinea pig serum (virus positive control) and wells that receive no virus (virus negative control). Cells and virus are incubated for 2 to 3 days at 37° C. before quantifying for viral cytopathic effect. The viral cytopathic effect is quantified by staining with 0.05% crystal violet followed by spectrophotometric absorbance measurements. The titer of interferon in serum is expressed as units/mL and is the reciprocal of the highest dilution that protects cells from virus.

Results are shown in the table below.

| Antiviral Activity and Interferon Induction in Guinea Pigs | | | |
|---|---|---|---|
| Compound of Example | Reference Units/mL | Dose mg/kg | % Lesion Inhibition |
| 9 | 2 | 37% | 266 |
| 10 | 0.5 | 29% | not run |
| 11 | 1 | 100% | >12,800 |
| 11 | 0.5 | 100% | >12,800 |
| 11 | 0.1 | 50% | not run |
| 12 | 2 | 100% | >12,800 |
| 12 | 0.5 | 82% | >12,800 |
| 13 | 2 | 67% | not run |
| 20 | 2 | 100% | not run |

These results show that the tested compounds of the invention inhibit Herpes simplex virus type II lesions in guinea pigs. Those compounds tested were also shown to induce interferon biosynthesis in guinea pigs.

INTERFERON-α INDUCTION IN HUMAN CELLS

The test methods described below demonstrate the ability of compounds of the invention to induce the biosynthesis of interferon-α in human cells.

An in vitro human blood cell system was used to assess interferon-α induction by compounds of the invention. Activity is based on the measurement of interferon secreted into culture medium. Interferon is measured by bioassay.

Blood Cell Preparation for Culture

Whole blood is collected by venipuncture into EDTA vacutainer tubes. Peripheral blood mononuclear cells (PBM) are prepared by LeucoPREP™ Brand Cell Separation Tubes (available from Becton Dickinson) and cultured in RPMI 1640 medium (available from GIBCO, Grand Island, N.Y.) containing 25 mM HEPES 4-(2-hydroxyethylpiperazine-N'-2-ethanesulfonic acid and L-glutamine (1% penicillin-streptomycin solution added) with 10% autologous serum added. Alternatively, whole blood diluted 1:10 with RPMI 1640 medium supplemented with 25 mM HEPES and L-glutamine with 1% penicillin-streptomycin solution added can be used. 200 μL portions of diluted whole blood or of PBM in medium are added to 96 well (flat bottom) MicroTest™III tissue culture plates.

Compound Preparation

The compounds are solubilized in water, ethanol, or dimethyl sulfoxide then diluted with distilled water, 0.01N sodium hydroxide or 0.01N hydrochloric acid. (The choice of solvent will depend on the chemical characteristics of the compound being tested.) Compounds are initially tested in a concentration range of from about 0.1 μg/mL to about 5 μg/mL. Compounds that show induction at a concentration of 0.5 μg/mL are then tested in a concentration range of 0.01 μg/mL to 5.0 μg/mL.

Incubation

The solution of test compound is added (in a volume less than or equal to 50 μL) to the wells containing 200 μL of PBM in medium or diluted whole blood. Solvent and/or medium is added to control wells (i.e., wells with no test compound) and also as needed to adjust the final volume of each well to 250 μL. The plates are covered with plastic lids, vortexed gently and then incubated for 24 hours at 37° C. with a 5% carbon dioxide atmosphere.

Separation

Following incubation, the plates are covered with PARAFILM™ and then centrifuged at 1000 rpm for 15 minutes at 4° C. in a Damon IEC Model CRU-5000 centrifuge. Medium (about 175 μL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis. The details of the bioassay method are described by G. L. Brennan and L. H. Kronenberg in "Automated Bioassay of Interferons in Micro-test Plates", Biotechniques, June/July; 78, 1983, incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as α interferon reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus. Results are shown in the table below wherein the absence of an entry indicates that the compound was not tested at the particular dose concentration. Results designated as "<" a certain number indicate that interferon was not detectable in amounts above the lower sensitivity level of the assay.

| Interferon-α Induction in Human Cells | | | | | | | |
|---|---|---|---|---|---|---|---|
| Compound | α Reference Units/mL Dose Concentration (μg/mL) | | | | | | Cell |
| of Example | 0.01 | 0.05 | 0.10 | 0.50 | 1.0 | 5.0 | Type |
| 9 | <1.8 | 16 | 140 | 750 | 750 | 750 | PBM |
| 10 | — | — | <1.5 | 96 | 120 | 120 | whole blood |
| 10 | <1.3 | 28 | 140 | 750 | 750 | 190 | PBM |
| 11 | — | — | 330 | 330 | 250 | 140 | whole blood |
| 11 | 330 | 330 | 570 | 570 | 570 | 570 | PBM |
| 12 | — | — | <1.8 | 37 | 140 | 330 | whole blood |
| 13 | — | — | <1.9 | 10 | 10 | 4 | PBM |
| 15 | — | — | <1.8 | 250 | 430 | 750 | PBM |
| 20 | — | — | 85 | 440 | 250 | 190 | whole blood |
| 20 | <1.8 | 190 | 190 | 1000 | 1000 | 1000 | PBM |
| 23 | — | — | <1.8 | <1.8 | 84 | 250 | whole blood |
| 27 | <4 | 24 | 3300 | 550 | 370 | 490 | PBM |
| 29 | — | — | <5.4 | 440 | 1000 | 580 | PBM |
| 30 | — | — | <4 | <4 | <4 | 72 | PBM |
| 31 | <4 | 18 | 2500 | 370 | 280 | 370 | PBM |
| 34 | <4 | <4 | 1600 | 550 | 180 | 200 | PBM |
| 37 | — | — | <4 | 2500 | 2500 | 210 | PBM |
| 40 | — | — | 680 | 230 | 210 | 210 | PBM |
| 44 | — | — | 3000 | 430 | 430 | 760 | PBM |
| 48 | — | — | 3100 | 840 | 330 | 1300 | PBM |
| 51 | — | — | <5 | <5 | 1000 | 330 | PBM |
| 55 | — | — | <4 | 1500 | 1500 | 490 | PBM |
| 60 | — | — | 1700 | 430 | 570 | 570 | PBM |
| 61 | — | — | 64 | 1300 | 330 | 330 | PBM |
| 62 | — | — | <5 | <5 | 31 | 760 | PBM |
| 66 | — | — | <5 | <5 | 1000 | 1000 | PBM |
| 69 | <6.4 | <6.4 | 1000 | 680 | 390 | 900 | PBM |

-continued

| Interferon-α Induction in Human Cells | | | | | | | |
|---|---|---|---|---|---|---|---|
| Compound | α Reference Units/mL Dose Concentration (μg/mL) | | | | | | Cell |
| of Example | 0.01 | 0.05 | 0.10 | 0.50 | 1.0 | 5.0 | Type |
| 72 | — | — | 200 | 210 | 220 | 420 | PBM |
| 77 | <6.3 | <6.3 | 2600 | 390 | 250 | 280 | PBM |
| 81 | — | — | 1100 | 2200 | 460 | 1100 | PBM |
| 85 | — | — | 86 | 100 | 220 | 230 | PBM |
| 90 | <6.4 | 640 | 3000 | 640 | 420 | 580 | PBM |
| 93 | — | — | 850 | 280 | 300 | 300 | PBM |
| 96 | <6.4 | 44 | 1200 | 460 | 1000 | 900 | PBM |
| 99 | 28 | 316 | 280 | 790 | 790 | 630 | PBM |
| 104 | <2.7 | <2.7 | 310 | 180 | 140 | 310 | PBM |
| 109 | <1.4 | 1000 | 1000 | 97 | 83 | 78 | PBM |
| 111 | 190 | 65 | 65 | 49 | 55 | 61 | PBM |
| 115 | 91 | 96 | 120 | 190 | 190 | 240 | PBM |
| 117 | <4.4 | 360 | 340 | 140 | 91 | 110 | PBM |

These results show that the tested compounds of the invention induce interferon biosynthesis at detectable levels in human whole blood and/or PBM cells over a wide range of dose concentrations.

INTERFERON INDUCTION IN MICE

The test methods described below demonstrate the ability of compounds of the invention to induce interferon biosynthesis in mice.

For each dose level being tested, three groups (three mice per group) of CFW male mice (nonfasted; weighing 23–28 g) are dosed orally with compound. One hour later blood samples are withdrawn from the first group. The samples are pooled then centrifuged. The serum is removed from the centrifuge tube, split into two portions, then placed in freezing vials and maintained at −70° C. until analysis. This procedure is repeated at 2 hours with the second group of mice and at 4 hours with the third group of mice.

Interferon Analysis/Calculation

Samples are assayed as described above in connection with the analysis of interferon induction in human cells. The results are expressed in the table below as α/β reference units/mL based on the value obtained for a mouse MU-i-IF standard. Results are shown in the table below wherein results designated as "<" a certain number indicate that interferon was not detectable in amounts above the lower sensitivity level of the assay.

| Interferon Induction in Mice | | | | |
|---|---|---|---|---|
| Compound of | Dose | Reference Units/mL | | |
| Example | mg/kg | 1 hr | 2 hr | 4 hr |
| 9 | 30 | 2900 | 5000 | 4 |
| 9 | 10 | 330 | 740 | ≦47 |
| 9 | 3 | ≦47 | ≦47 | <47 |
| 9 | 1 | <47 | <47 | <47 |
| 10 | 10 | <120 | <120 | 600 |
| 10 | 3 | <120 | <120 | <120 |
| 10 | 1 | <120 | <120 | <120 |
| 10 | 0.3 | <120 | <120 | <120 |
| 11 | 30 | 850 | 2500 | 40 |
| 11 | 10 | 1100 | 2500 | 280 |
| 11 | 3 | 490 | 1900 | 30 |
| 11 | 1 | 280 | 1100 | 71 |
| 12 | 30 | 850 | 5800 | 40 |
| 12 | 10 | 850 | 850 | 40 |
| 12 | 3 | 54 | 40 | <18 |
| 12 | 1 | 94 | 160 | <18 |

| Compound of Example | Dose mg/kg | 1 hr | 2 hr | 4 hr |
|---|---|---|---|---|
| 13 | 10 | 700 | 1200 | 400 |
| 13 | 3 | 230 | 400 | 130 |
| 13 | 1 | 130 | 530 | ≦100 |
| 13 | 0.3 | <59 | ≦130 | <59 |
| 15 | 10 | 270 | 3100 | 270 |
| 15 | 3 | <120 | 270 | <120 |
| 15 | 1 | <120 | <120 | <120 |
| 15 | 0.3 | <120 | <120 | <120 |
| 20 | 30 | 2200 | 8700 | 320 |
| 20 | 10 | 2200 | 5000 | 100 |
| 20 | 3 | 970 | 1200 | 140 |
| 20 | 1 | 140 | 560 | <47 |
| 23 | 30 | 1200 | 1200 | 140 |
| 27 | 10 | 130 | 690 | <45 |
| 27 | 3 | <59 | 230 | <45 |
| 27 | 1 | <45 | <45 | <45 |
| 27 | 0.3 | <45 | <45 | <45 |
| 29 | 10 | <45 | <45 | <45 |
| 29 | 3 | <45 | <45 | <45 |
| 29 | 1 | <45 | <45 | <45 |
| 29 | 0.3 | <45 | <45 | <45 |
| 30 | 10 | <120 | 600 | <120 |
| 30 | 3 | <120 | <120 | <120 |
| 30 | 1 | <120 | <120 | <120 |
| 30 | 0.3 | <120 | <120 | <120 |
| 31 | 10 | 960 | 5000 | 550 |
| 31 | 3 | 420 | 420 | 320 |
| 31 | 1 | <61 | 140 | ≦61 |
| 31 | 0.3 | <61 | <61 | <61 |
| 34 | 10 | 1100 | 1100 | 180 |
| 34 | 3 | 420 | 420 | 140 |
| 34 | 1 | 140 | 320 | ≦61 |
| 34 | 0.3 | ≦61 | ≦61 | ≦61 |
| 37 | 10 | 270 | ≦270 | ≦270 |
| 37 | 3 | <120 | <120 | <120 |
| 37 | 1 | <120 | <120 | <120 |
| 37 | 0.3 | <120 | <120 | <120 |
| 60 | 10 | 870 | 3400 | 1100 |
| 60 | 3 | 380 | 870 | 290 |
| 60 | 1 | 290 | 1500 | 120 |
| 60 | 0.3 | 120 | 870 | ≦56 |
| 61 | 10 | 290 | 1100 | 160 |
| 61 | 3 | 290 | 500 | 120 |
| 61 | 1 | 120 | 220 | 97 |
| 61 | 0.3 | <56 | <56 | <56 |
| 62 | 10 | 380 | 1100 | 380 |
| 62 | 3 | 220 | 870 | 160 |
| 62 | 1 | <56 | 97 | <56 |
| 62 | 0.3 | <56 | <56 | <56 |
| 66 | 10 | 1100 | 2600 | 380 |
| 66 | 3 | <74 | <120 | <56 |
| 66 | 1 | <56 | <56 | <56 |
| 66 | 0.3 | <56 | <56 | <56 |
| 40 | 10 | 1600 | 1600 | 170 |
| 40 | 3 | 990 | 1100 | 210 |
| 40 | 1 | 450 | 450 | 110 |
| 40 | 0.3 | 450 | 200 | <29 |
| 44 | 10 | 1800 | 1600 | 790 |
| 44 | 3 | 1000 | 1500 | <260 |
| 44 | 1 | 990 | <260 | <260 |
| 44 | 0.3 | ⁻570 | 510 | <260 |
| 48 | 10 | 2000 | 2000 | ⁻540 |
| 48 | 3 | 1600 | 1600 | ⁻510 |
| 48 | 1 | 790 | 940 | <260 |
| 48 | 0.3 | <260 | <260 | <260 |
| 69 | 10 | 1000 | 1000 | ≦340 |
| 69 | 3 | ≦270 | ≦150 | <150 |
| 69 | 1 | <150 | <150 | <150 |
| 69 | 0.3 | <150 | <150 | <150 |
| 85 | 10 | 2200 | 5700 | ⁻570 |
| 85 | 3 | 1500 | 4300 | ⁻430 |
| 85 | 1 | ⁻980 | 3900 | ≦330 |
| 85 | 0.3 | 670 | 670 | <250 |
| 90 | 10 | 750 | 3500 | ≦140 |
| 90 | 3 | ≦130 | 570 | ≦74 |
| 90 | 1 | <74 | <74 | <74 |
| 90 | 0.3 | <74 | <74 | <74 |
| 93 | 10 | 2100 | 2900 | 630 |
| 93 | 3 | 1300 | 1300 | ⁻260 |
| 93 | 1 | 660 | 1500 | 340 |
| 93 | 0.3 | 400 | 360 | ≦150 |
| 96 | 10 | 2900 | 4700 | ⁻350 |
| 96 | 3 | 3000 | 10000 | 960 |
| 96 | 1 | 3200 | 5000 | 1100 |
| 96 | 0.3 | 2900 | 3400 | 620 |
| 99 | 10 | 2500 | 4600 | ⁻220 |
| 99 | 3 | 1600 | 750 | ⁻220 |
| 99 | 1 | 2200 | 5100 | 460 |
| 99 | 0.3 | 1600 | 3500 | 390 |
| 104 | 10 | 3400 | 4500 | ≦660 |
| 104 | 3 | ≦660 | 2200 | <380 |
| 104 | 1 | ⁻780 | ⁻780 | ⁻380 |
| 104 | 0.3 | <380 | <380 | <380 |
| 115 | 10 | 5600 | 5300 | 870 |
| 115 | 3 | 2200 | 5300 | ⁻310 |
| 115 | 1 | 1400 | 2900 | ⁻310 |
| 115 | 0.3 | ⁻380 | 2500 | ⁻360 |
| 117 | 10 | 1100 | 480 | ⁻310 |
| 117 | 3 | ⁻820 | 2200 | ⁻310 |
| 117 | 1 | ≦270 | 630 | ≦270 |
| 117 | 0.3 | <160 | 1200 | <160 |

These results show that the tested compounds induce interferon biosynthesis at detectable levels in mice.

INHIBITION OF MC-26 TUMORS IN MICE

The test methods described below demonstrate the ability of compounds of the invention to inhibit tumor growth in mice.

On day 0 female CDF1 mice are inoculated i.v. with $4 \times 10^4$ MC-26 colon tumor cells in a volume of 0.2 ml of saline per mouse. The mice are sacrificed 14 days later. The lungs are removed and fixed with WARF (24% ethanol, 10% formalin, and 2% acetic acid in water) then allowed to stand for 30 minutes. The lobes are separated and the colonies are counted. Five mice are in each treatment group and comparisons are made to controls.

The mice in the treatment groups were dosed on days 3, 4, 5, 6, 7, 10, 11, 12, 13, and 14, orally with a suspension of compound (30 mg/kg) in water (10 mL/kg).

The mice in the control groups were dosed orally with saline (10 mL/kg) on days 3, 4, 5, 6, and 7, and with water (10 mL/kg) on days 10, 11, 12, 13, and 14.

Results are shown in the table below.

| Compound of Example | Number of Colonies |
|---|---|
| 11 | 204 ± 28 |
| 12 | 149 ± 21 |
| 31 | 221 ± 37 |
| 34 | 196 ± 20 |
| 37 | 123 ± 31 |
| Control | 385 ± 31 |

On day 0 female CDF1 mice are inoculated i.v. with $1 \times 10^4$ MC-26 colon tumor cells in a volume of 0.2 mL of saline per mouse. The mice are sacrificed 21 days later. The lungs are removed and fixed with WARF then allowed to stand for 30 minutes. The lobes are separated and the colonies are counted. Ten mice are in each treatment group and in the control group.

The mice in the control group were dosed orally with water (10 mL/Kg) on days 0, 1, 2, 3 and 4. Four mice from this group died prior to day 21.

The mice in the first treatment group were dosed on days 0, 1, 2, 3 and 4 orally with a suspension of the compound of Example 99 (1 mg/Kg) in water (10 mL/Kg). One mouse from this group died prior to day 21.

The mice in the second treatment group were dosed on days 0, 1, 2, 3 and 4 orally with a suspension of the compound of Example 99 (3 mg/Kg) in water (10 mL/Kg). All of the mice in this treatment group survived until day 21.

Results are shown in the table below.

| Inhibition of MC-26 Tumors in Mice | | |
|---|---|---|
| Treatment | N | Number of Colonies |
| 3 mg/Kg | 10 | 17 ± 3 |
| 1 mg/Kg | 9 | 29 ± 4 |
| Control | 6 | 55 ± 11 |

These results show that the tested compounds inhibit MC-26 tumor formation in mice.

INDIRECT IN-VITRO ANTIVIRAL ACTIVITY

The test method described below demonstrates the ability of compounds of the invention to inhibit the progress of viral infection.

Whole blood is collected by venipuncture into EDTA vacutainer tubes. Peripheral blood mononuclear cells (PBM) are isolated using Ficoll-Paque® solution (available from Pharmacia LKB Biotechnology Inc., Piscataway, N.J.). The PBM are washed with phosphate buffer saline then diluted with RPMI 1640 medium (available form GIBCO, Grand Island, New York) to obtain a final concentration of $2.5 \times 10^6$ cells/mL. One mL portions of PBM in medium are placed in 15 mL polypropylene tubes. A 100 μL portion of autologous serum is added to each tube. The test compound is dissolved in dimethyl sulfoxide then diluted with RPMI 1640 medium. The solution of test compound is added to the tubes containing the PBM to give final concentrations ranging from 0.1 μg/mL to 10 μg/mL. Control tubes do not receive any test compound. The tubes are then incubated for 24 hours at 37° C. with a 5% carbon dioxide atmosphere. Following incubation the tubes are centrifuged at 400× g for 5 minutes. The supernatant is removed. The PBM's are brought up in 100 μL of RPMI 1640 medium and then infected with a 100 μL containing $10^5$ tissue culture 50% infectious doses of vesicular stomatitis virus (VSV). The tubes are incubated for 30 minutes at 37° C. to allow virus adsorption. One mL of RPMI 1640 medium is added to each tube and the tubes are incubated for 48 hours at 37° C. The tubes are frozen then thawed to lyse the cells. The tubes are centrifuged at 400× g for 5 minutes to remove cellular debris then the supernatant is assayed by serial tenfold dilutions on Vero cells in 96 well microtiter plates. The infected cells are incubated for 24 hours at 37° C. before quantifying for viral cytopathic effect. The viral cytopathic effect is quantified by staining with 0.05% crystal violet. Results are presented as VSV inhibition, defined as the $\log_{10}$ (control VSV yield/experimental VSV yield). Results are shown in the table below wherein the absence of an entry indicates that the compound was not tested at that particular dose concentration. Control tubes have a value of 0.

| | In-vitro Antiviral Activity | | | | |
|---|---|---|---|---|---|
| Compound of | VSV Yield Inhibition Dose Concentration (μg/mL) | | | | |
| Example | 10 | 5 | 1.0 | 0.5 | 0.1 |
| 15 | 5 | 5 | 6 | — | — |
| 27 | — | — | 4 | 3 | 4 |
| 31 | 6 | 5 | 5 | — | — |
| 40 | 6 | 7 | 7 | — | — |
| 44 | — | — | 7 | 4 | 3 |
| 51 | — | — | 5 | 1 | 0 |
| 61 | — | — | 5 | 7 | 5 |
| 66 | — | — | 3 | 2 | 2 |
| 72 | — | — | 5 | 5 | 5 |
| 77 | — | — | 5 | 5 | 3 |
| 81 | — | — | 5 | 4 | 5 |
| 85 | — | — | 5 | 5 | 5 |
| 90 | — | — | 5 | 4 | 5 |
| 93 | — | — | 5 | 5 | 0 |
| 96 | — | — | 5 | 5 | 6 |
| 99 | — | — | 5 | 5 | 5 |

These results show that the tested compounds are active against VSV.

We claim:

1. A compound of the formula:

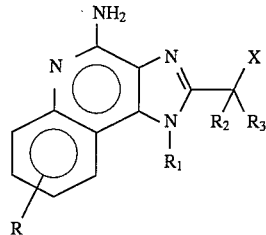

wherein $R_1$ is selected from the group consisting of hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_2$ and $R_3$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, hydroxyalkyl of one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, and alkylthio of one to about four carbon atoms; and R is selected from the group consisting of hydrogen, straight chain or branched chain alkoxy containing one to about four carbon atoms, halogen, and straight chain or branched chain alkyl containing one to about four carbon atoms;

or a pharmaceutically acceptable acid addition salt thereof:

with the proviso that when $R_1$ is selected from the group consisting of:

hydroxyalkyl of one to about six carbon atoms and alkoxyalkyl wherein the alkoxy moiety is of one to about four carbon atoms and the alkyl moiety is of one to about six carbon atoms; and $R_2$ and $R_3$ are independently selected from the group consisting of hydrogen and alkyl of one to about four carbon atoms;

then X is other than alkoxy of one to about four carbon atoms, alkoxyalkyl wherein the alkoxy moiety is of one to about four carbon atoms and the alkyl moiety is of one to about four carbon atoms, hydroxyalkyl of one to about four carbon atoms, and hydroxy.

2. A compound according to claim 1, wherein Rm contains from two to about ten carbon atoms.

3. A compound according to claim 1, wherein Rhd 1contains from two to about eight carbon atoms.

4. A compound according to claim 1, wherein $R_1$ is 2-hydroxy-2-methylpropyl or 2-methylpropyl.

5. A compound according to claim 1, wherein $R_1$ is benzyl.

6. A compound according to claim 1, wherein $R_1$ is alkoxyalkyl wherein the alkoxy moiety contains one to about four carbon atoms and the alkyl moiety contains two to about six carbon atoms.

7. A compound according to claim 6, wherein $R_1$ is methoxyethyl or 3-methoxypropyl.

8. A compound according to claim 1, wherein X is azido, ethoxy, hydroxy, methoxy, 1-morpholino, or methylthio.

9. A compound according to claim 1, wherein R is hydrogen.

10. A compound according to claim 1, wherein $R_2$ is hydrogen and $R_3$ is 4-chlorophenyl.

11. A compound according to claim 1, wherein $R_2$ is hydrogen and $R_3$ is methyl.

12. A compound according to claim 1, wherein $R_2$ and $R_3$ are methyl.

13. A compound according to claim 1, wherein $R_2$ and $R_3$ are hydrogen.

14. A compound according to claim 1, wherein $R_2$ is hydrogen and $R_3$ is n-butyl.

15. A compound according to claim 1, wherein $R_2$ is hydrogen and $R_3$ is phenyl.

16. A compound of the formula:

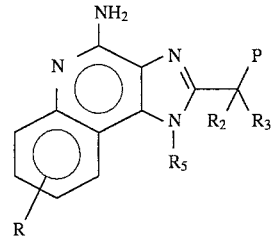

wherein $R_5$ is selected from the group consisting of: straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;

$R_2$ and $R_3$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

P is selected from the group consisting of alkanolyloxy, alkanoyloxyalkyl wherein the alkyl moiety contains one to about four carbon atoms, and aroyloxy; and R is selected from the group consisting of hydrogen, straight chain or branched chain alkoxy containing one to about four carbon atoms, halogen, and straight chain or branched chain alkyl containing one to about four carbon atoms.

17. A compound according to claim 16, wherein $R_5$ contains from two to about ten carbon atoms.

18. A compound according to claim 16, wherein $R_5$ contain from two to about eight carbon atoms.

19. A compound according to claim 16, wherein $R_5$ is 2-methylpropyl.

20. A compound according to claim 16, wherein $R_5$ is benzyl.

21. A compound according to claim 16, wherein $R_5$ is alkoxyalkyl wherein the alkoxy moiety contains one to about four carbon atoms and the alkyl moiety contains one to about six carbon atoms.

22. A compound according to claim 16, wherein $R_5$ is methoxyethyl or 3-methoxypropyl.

23. A compound according to claim 16, wherein P is acetoxy or benzoyloxy.

24. A compound according to claim 16, wherein R is hydrogen.

25. A compound according to claim 16, wherein $R_2$ is hydrogen and $R_3$ is 4-chlorophenyl.

26. A compound according to claim 16, wherein $R_2$ is hydrogen and $R_3$ is methyl.

27. A compound according to claim 16, wherein $R_2$ and $R_3$ are methyl.

28. A compound according to claim 16, wherein $R_2$ and $R_3$ are hydrogen.

29. A compound according to claim 16, wherein $R_2$ is hydrogen and $R_3$ is n-butyl.

30. A compound according to claim 16, wherein $R_2$ is hydrogen and $R_3$ is phenyl.

31. A compound according to claim 16, selected from the group consisting of 4-amino-α-methyl-1-(2-methylpropyl)-1H-imidazo[4,5-c]quinoline-2-methyl acetate and 4-amino-α-methyl-1-(2-methylpropyl)-1H-imidazo[4,5-c]quinoline-2-ethyl acetate.

32. An antiviral pharmaceutical composition comprising a compound according to claim 1 and a pharmaceutically acceptable vehicle, the compound being present in an amount effective to inhibit the progress of a viral infection.

33. A method of inducing interferon biosynthesis in a mammal, which method comprises administering to the mammal a compound according to claim 1 in an amount sufficient to induce interferon biosynthesis.

34. A compound according to claim 1, selected from the group consisting of:

N-acetyl-4-amino-1-(2-methylpropyl)-1H-imidazo[4,5-c]quinoline-2-methanamine;

4-amino-α-(4-chlorophenyl)-1-(2-methylpropyl)-1H-imidazo[4,5-c]quinoline-2-methanol;

4-amino-α,α-dimethyl-1-(2-methylpropyl)-1H-imidazo[4,5-c]quinoline-2-methanol;

4-amino-N-hydroxyethyl-N-methyl-1-phenylmethyl-1H-imidazo[4,5-c]quinoline-2-methanamine hemihydrate;

4-amino-α-methyl-1-(2-methylpropyl)-1H-imidazo[4,5-c]quinoline-2-ethanol;

4-amino-α-methyl-1-(2-methylpropyl)-1H-imidazo[4,5-c]quinoline-2-methanol;

4-amino-1-(2-methylpropyl)-1H-imidazo[4,5-c]quinoline-2-methanol;

4-amino-1-(2-methylpropyl)-α-phenyl-1H-imidazo[4,5-c]quinoline-2-methanol;

2-azidomethyl-1-(2-methylpropyl)-1H-imidazo[4,5-c]quinolin-4-amine;

2-chloromethyl-1-(2-methylpropyl)-1H-imidazo[4,5-c]quinolin-4-amine hydrochloride;

2-ethoxymethyl-1-(2-methylpropyl)-1H-imidazo[4,5-c]quinolin-4-amine;

2-ethoxymethyl-1-phenylmethyl-1H-imidazo[4,5-c]quinolin-4-amine;

2-(α-methoxybenzyl)-1-(2-methylpropyl)-1H-imidazo[4,5-c]quinolin-4-amine;

2-(2-methoxyethyl)-1-(2-methylpropyl)-1H-imidazo[4,5-c]quinolin-4-amine;

2-(1-methoxyethyl)-1-(2-methylpropyl)-1H-imidazo[4,5-c]quinolin-4-amine;

2-methoxymethyl-1-(2-methylpropyl)-1H-imidazo[4,5-c]quinolin-4-amine;

2-methoxymethyl-1-phenylmethyl-1H-imidazo[4,5-c]quinolin-4-amine;

2-(1-methoxypentyl)-1-(2-methylpropyl)-1H-imidazo[4,5-c]quinolin-4-amine;

2-(2-methoxypropyl)-1-(2-methylpropyl)-1H-imidazo[4,5-c]-4-amine;

1-(2-methylpropyl)-2-morpholinomethyl-1H-imidazo[4,5-c]quinolin-4-amine;

1-(2-methylpropyl)-2-pyrrolidinomethyl-1H-imidazo[4,5-c]quinolin-4-amine;

2-methylthiomethyl-1-phenylmethyl-1H-imidazo[4,5-c]quinolin-4-amine;

2-morpholinomethyl-1-phenylmethyl-1H-imidazo[4,5-c]quinolin-4-amine; and

2-[1-(1-morpholino)pentyl]-1-(2-methylpropyl)-1H-imidazo[4,5-c]quinolin-4-amine.

35. A compound according to claim 1, selected from the group consisting of:

4-amino-α-butyl-1-(2-methylpropyl)-1H-imidazo[4,5-c]quinoline-2-methanol; and 4-amino-1-phenylmethyl-1H-imidazo[4,5-c]quinoline-2-methanol.

36. A compound according to claim 1, selected from the group consisting of 2-ethoxymethyl-1-(3-methylbutyl)-1H-imidazo[4,5-c]quinolin-4-amine, 1-butyl-2-methoxyethyl-1H-imidazo[4,5-c]quinolin-4-amine, 1-butyl-2-ethoxymethyl-1H-imidazo[4,5-c]quinolin-4-amine, and 4-amino-1-butyl-1H-imidazo[4,5-c]quinoline-2-methanol, or a pharmaceutically acceptable acid addition salt thereof.

* * * * *

UNITED STATES PATENT AND TRADEMARK OFFICE
CERTIFICATE OF CORRECTION

PATENT NO.: 5,605,899

DATED: February 25, 1997

INVENTOR(S): John F. Gerster, et al.

It is certified that error appears in the above-identified patent and that said Letters Patent is hereby corrected as shown below:

Column 49, line 30, "thereof:" should be --thereof;--;

Column 49, line 46, "Rm" should be --$R_1$--; and

Column 49, lines 48 and 49, "Rhd 1contains" should be --$R_1$ contains--.

Signed and Sealed this

Eighth Day of September, 1998

Attest:

Attesting Officer

BRUCE LEHMAN

Commissioner of Patents and Trademarks